(12) United States Patent
Kikuchi et al.

(10) Patent No.: US 9,339,454 B2
(45) Date of Patent: May 17, 2016

(54) SKIN WHITENING AGENT

(75) Inventors: Mamiko Kikuchi, Utsunomiya (JP); Daiki Murase, Mason, OH (US); Mitsuru Sugiyama, Utsunomiya (JP); Akiko Kawasaki, Utsunomiya (JP)

(73) Assignee: Kao Corporation, Tokyo (JP)

( * ) Notice: Subject to any disclaimer, the term of this patent is extended or adjusted under 35 U.S.C. 154(b) by 1 day.

(21) Appl. No.: 13/979,991

(22) PCT Filed: Jan. 20, 2012

(86) PCT No.: PCT/JP2012/051242
§ 371 (c)(1),
(2), (4) Date: Jul. 16, 2013

(87) PCT Pub. No.: WO2012/099247
PCT Pub. Date: Jul. 26, 2012

(65) Prior Publication Data
US 2013/0295207 A1    Nov. 7, 2013

(30) Foreign Application Priority Data

Jan. 21, 2011 (JP) ................................. 2011-010603
Sep. 1, 2011 (JP) ................................. 2011-190517

(51) Int. Cl.
| A61K 36/00 | (2006.01) |
| A61K 8/97 | (2006.01) |
| A61K 31/365 | (2006.01) |
| A61K 36/19 | (2006.01) |
| A61K 8/49 | (2006.01) |
| A61Q 19/02 | (2006.01) |
| A61K 8/60 | (2006.01) |
| A61K 31/7048 | (2006.01) |
| A23L 1/30 | (2006.01) |

(52) U.S. Cl.
CPC ............. *A61K 8/97* (2013.01); *A23L 1/3002* (2013.01); *A61K 8/4973* (2013.01); *A61K 8/602* (2013.01); *A61K 31/365* (2013.01); *A61K 31/7048* (2013.01); *A61K 36/19* (2013.01); *A61Q 19/02* (2013.01); *A61K 2800/782* (2013.01)

(58) Field of Classification Search
None
See application file for complete search history.

(56) References Cited

U.S. PATENT DOCUMENTS

2010/0105769 A1* 4/2010 Nho .................. A61K 36/75
514/464

FOREIGN PATENT DOCUMENTS

| CN | 1778378 A | * | 5/2006 |
| CN | 1935228 A | * | 3/2007 |
| CN | 101102744 A | | 1/2008 |
| CN | 101433255 A | * | 5/2009 |
| JP | 63-146845 A | | 6/1988 |
| JP | 04211609 A | * | 8/1992 |
| JP | 09-012592 A | | 1/1997 |
| JP | 09-030946 A | | 2/1997 |
| JP | 3099243 B | | 8/2000 |
| JP | 2002-114629 A | | 4/2002 |
| JP | 2003-089630 A | | 3/2003 |
| JP | 2006-225286 A | | 8/2006 |
| JP | 2007-261987 A | | 10/2007 |
| JP | 2010-116371 A | | 5/2010 |
| JP | 2010-159221 A | | 7/2010 |
| JP | 2010-195731 A | | 9/2010 |
| WO | WO 2006/068254 A1 | | 6/2006 |
| WO | WO 2008/058897 A2 | | 5/2008 |

OTHER PUBLICATIONS

Schinella et al, On the preclinical anti-trypanosomal, anti-inflammatory and toxicological activities of H. linifolium (L.) G. Don and diphyllin derivatives. Boletin Latinoamericano y del Caribe de Plantas Medicinales y Aromaticas (2008), 7(4), 225-22/.*
Prieto et al, Topical anti-inflammatory lignans from Haplophyllum hispanicum. Z. Naturforsch. 51c: 618-22, 1996.*
Wang, C-C et al., "Constituents of *Peritrophe japonica* (Thunb.) Bremk," Journal of the Chinese Chemical Society, Aug. 1992, 39(4), pp. 351-353, The Chemical Society, Taipei.
Ohta, N et al., Overview of research on transcriptional regulation of tyrosinase family genes and the development of new skin-lightening agents, Fragrance Journal, Sep. 2000, pp. 24-30, Fureguransujanaru Co. Inc., Japan.

(Continued)

*Primary Examiner* — Qiuwen Mi
(74) *Attorney, Agent, or Firm* — Sterne, Kessler, Goldstein & Fox P.L.L.C.

(57) ABSTRACT

The invention provides a method for inhibiting dopa oxidase activity, for inhibiting melanin production, or for whitening skin using haguro-so or an organic solvent extract thereof, or a compound of formula (I):

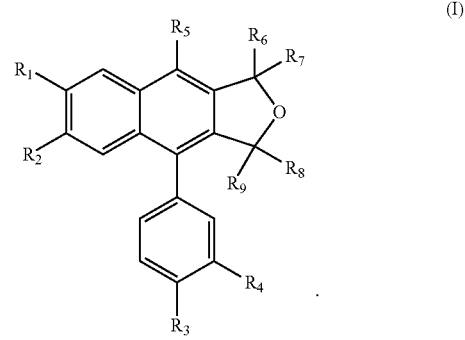

(I)

24 Claims, 3 Drawing Sheets

(56) References Cited

OTHER PUBLICATIONS

International Search Report (ISR) for PCT/JP2012/051242; I.A. fd: Jan. 20, 2012, mailed Mar. 13, 2012 from the Japanese Patent Office, Tokyo, Japan.

International Preliminary Report on Patentability (IPRP), Chapter I of the Patent Cooperation Treaty, including the Written Opinion for PCT/JP2012/051242; I.A. fd: Jan. 20, 2012, issued Jul. 30, 2013, by the International Bureau of WIPO, Geneva, Switzerland.

Sánchez-Ferrer, A et al., "Tyrosinase: a comprehensive review of its mechanism," Biochim Biophys Acta 1247(1): 1-11 (Feb. 1995), Elsevier Pub. Co., Amsterdam, Netherlands.

"Whitening strategy. External preparation for whitening," in Advanced Cosmetic Dermatology, IV. Clinical pharmacology of skin whitening agent ("Bihaku senryaku, IV. Bihakuzaino yakuri to rinsho"), Y. Miyachi et al., eds., Nankodo Co., Ltd, Japan pp. 99-101 (2006).

Innocenti, G et al., "Patavine, a new arylnaphthalene lignan glycoside from shoot cultures of *Haplophyllum patavinum*," Chem Pharm Bull (Tokyo), 50(6): 844-846, (Jun. 2002), Pharmaceutical Society of Japan, Tokyo, Japan.

Govindachari, TR et al., "Chemical constituents of *Cleistanthus collinus* (RoxB.)," Tetrahedron 25:2815-2821 (1969), Pergamon Press, Great Britain.

Asano, J et al., "Antiviral activity of lignans and their glycosides from *Justicia procumbens*," Phytochemistry 42(3): 713-717, (Jun. 1996), Pergamon Press, London, Great Britain.

Lee, J-C et al., "Justicidin A decreases the level of cytosolic Ku70 leading to apoptosis in human colorectal cancer cells," Carcinogenesis 26: 1716-1730, (Oct. 2005), Oxford University Press, Oxford, England.

Kagan, VE et al., "Ascorbate is the primary reductant of the phenoxyl radical of etoposide in the presence of thiols both in cell homogenates and in model systems," Biochemistry 33(32): 9651-9660, (Aug. 1994), American Chemical Society, Washington, DC.

Parasuraman S, et al., "Computer-aided prediction of biological activity spectra, pharmacological and toxicological properties of cleistanthin A and B,". International Journal of Research in Pharmaceutical Sciences 1(3): 333-337 (2010), JK Welfare & Pharrnascope Foundation, India.

\* cited by examiner

SKIN WHITENING AGENT

FIELD OF THE INVENTION

The present invention relates to a skin whitening agent, a melanin production inhibitor, or a dopa oxidase activity inhibitor.

BACKGROUND OF THE INVENTION

Cosmetically the white skin with little pigmentation, speckle, or freckle appears to be favored, for this reason a substance having a skin whitening effect and very safe even when used for an extended time is in demand.

The pigmentation, speckles, freckles, and the like, are generally considered to be caused as a result of the melanin production enhanced by the activated melanocyte present in the skin due to the stimulation from skin exposure to ultraviolet ray, hormonal imbalance, genetic factors, or the like. The mechanism of melanin production enhancement is complicated but it is known that melanin is biosynthesized by the enzyme tyrosinase activity and the dopa oxidase activity of tyrosinase is deeply involved with the melanin production mechanism (Non Patent Document 1).

Skin whitening agents targeting this melanin production mechanism have been developed. For example, ascorbic acid, arbutin, kojic acid, and the like, have been reported as skin whitening agents having an effect for inhibiting the melanin production by inhibiting the enzyme tyrosinase activity (Non Patent Document 2).

Further, plant extracts having a skin whitening effect and inhibiting the dopa oxidase activity have been reported. Examples include toosendan (*Melia toosendan* Sieb. et Zucc.), souka (*Amomum tsao-ka* Crevost et Lemaire), seneshio gurashirisu (*Senecio gracilis*) and kokurirc (*Veratrum nigrum* L.) (Patent Document 1), garden angelica (*Angelica archangelica*), flowering dogwood (*Benthamidia florida*), kansui (*Euphorbia kansui* Liou), Japanese sumac (*Rhus chinensis* Mill.), okazeri (*Cnidium monnieri* (L.) Cuss.), hairvein agrimony (*Agrimonia pilosa* Ledeb.), rouro (*Diuranthera minor* (C. H. Wright) Hemsl.), and common barberry (*Berberis aristata*) (Patent Document 2), inukaramatsu (*Pseudolarix amabilis*), true indigo (*Indigofera tinctoria*) and devil's trumpet (*Datura metel*) (Patent Document 3), and pomegranate (*Punica granatum*) flower (Patent Document 4).

However, a more effective skin whitening agent is expected to be developed.

Haguro-so (*Peristrophe japonica*) is a plant belonging to the Family Acanthaceae, Genus *Peristrophe*. A composition comprising plants belonging to the Family Acanthaceae including Genus *Peristrophe* is known for preventing and ameliorating metabolic syndrome (Patent Document 5). However, it is not known that these plants have skin whitening effects, melanin production inhibitory effects, or dopa oxidase activity inhibitory effects.

Arylnaphthalene lignans are known to be isolated from plants such as *Haplophyllum patavinum* or *Cleistanthus collinus* (Non Patent Documents 3 and 4). As the physiological activities rendered by arylnaphthalene lignans, justicidin A, justicidin B, diphyllin, and tuberculatin are known to have bone resorption activity, antiviral activity, or antitumor activity (Non Patent Documents 5 and 6) as well as justicidin A and cleistanthin A are known to have antitumor activity (Non Patent Documents 7 and 8, and Patent Document 6), and the like. However, it has not been known that these and other arylnaphthalene lignans have skin whitening effects and melanin production inhibitory effects.

CITATION LIST

Patent Document

Patent Document 1: JP-A-2010-195732
Patent Document 2: JP-A-2010-195731
Patent Document 3: JP-A-2010-159221
Patent Document 4: JP-A-2006-225286
Patent Document 5: JP-A-2010-116371
Patent Document 6: JP-B-3099243

Non Patent Document

Non Patent Document 1: Biochimica et Biophysica Acta, 1995, 1247: 1-11
Non Patent Document 2: Advanced Cosmetic Dermatology, TV. Clinical pharmacology of skin whitening agent ("Bihaku senryaku, IV. Bihakuzaino yakuri to rinsho" in Japanese) NANKODO Co., Ltd., p. 95-116
Non Patent Document 3: Chem. Pharm. Bull., 2002, 50: 844-846
Non Patent Document 4: Tetrahedron, 1969, 25: 2815-2821
Non Patent Document 5: Phytochemistry, 1996, 42: 713-717
Non Patent Document 6: Carcinogenesis, 2005, 26: 1716-1730
Non Patent Document 7: Biochemistry, 1994, 33: 9651-9660
Non Patent Document 8: International Journal of Research in Pharmaceutical Sciences, 2010, 1(3): 333-337

SUMMARY OF THE INVENTION

More specifically, the present invention provides a dopa oxidase activity inhibitor comprising haguro-so or an organic solvent extract thereof as an active ingredient.

The present invention also provides a melanin production inhibitor comprising haguro-so or an organic solvent extract thereof as an active ingredient.

The present invention also provides a skin whitening agent comprising haguro-so or an organic solvent extract thereof as an active ingredient.

The present invention also provides an external agent for the skin comprising haguro-so or an organic solvent extract thereof as an active ingredient.

Alternatively, the present invention provides a dopa oxidase activity inhibitor comprising as an active ingredient a compound represented by the following formula (I) or a salt thereof:

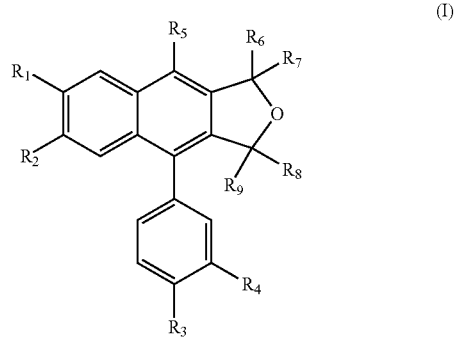

wherein, $R_1$ and $R_2$, being the same or different, each represent a hydroxyl group, or a $C_{1-4}$ linear or branched alkoxy group, or $R_1$ and $R_2$ together form a methylenedioxy group;

$R_3$ and $R_4$, being the same or different, each represent a hydroxyl group, or a $C_{1-4}$ linear or branched alkoxy group, or $R_3$ and $R_4$ together form a methylenedioxy group;

$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy, and (3-O-methyl-β-D-glucopyranosyl)oxy, and $R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

The present invention also provides a melanin production inhibitor comprising a compound represented by the above formula (I) (wherein $R_1$ to $R_9$ are as defined above) or a salt thereof as an active ingredient.

The present invention also provides a skin whitening agent comprising a compound represented by the above formula (I) (wherein $R_1$ to $R_9$ are as defined above) or a salt thereof as an active ingredient.

The present invention further provides use of haguro-so or an organic solvent extract thereof for dopa oxidase activity inhibition.

The present invention also provides use of haguro-so or an organic solvent extract thereof for melanin production inhibition.

The present invention also provides use of haguro-so or an organic solvent extract thereof for skin whitening.

The present invention also provides use of haguro-so or an organic solvent extract thereof for the external skin.

Alternatively, the present invention provides use of a compound represented by the above formula (I) (wherein $R_1$ to $R_9$ are as defined above) or a salt thereof for dopa oxidase activity inhibition.

The present invention also provides use of a compound represented by the above formula (I) (wherein $R_1$ to $R_9$ are as defined above) or a salt thereof for melanin production inhibition.

The present invention also provides use of a compound represented by the above formula (I) (wherein $R_1$ to $R_9$ are as defined above) or a salt thereof for skin whitening.

The present invention further provides use of haguro-so or an organic solvent extract thereof for producing a dopa oxidase activity inhibitor.

The present invention also provides use of haguro-so or an organic solvent extract thereof for producing a melanin production inhibitor.

The present invention also provides use of haguro-so or an organic solvent extract thereof for producing a skin whitening agent.

The present invention also provides use of haguro-so or an organic solvent extract thereof for producing an external agent for the skin.

Alternatively, the present invention provides use of a compound represented by the above formula (I) (wherein $R_1$ to $R_9$ are as defined above) or a salt thereof for producing a dopa oxidase activity inhibitor.

The present invention also provides use of a compound represented by the above formula (I) (wherein $R_1$ to $R_9$ are as defined above) or a salt thereof for producing a melanin production inhibitor.

The present invention also provides use of a compound represented by the above formula (I) (wherein $R_1$ to $R_9$ are as defined above) or a salt thereof for producing a skin whitening agent.

The present invention further provides a method for inhibiting a dopa oxidase activity in a subject comprising administration or ingestion of haguro-so or an organic solvent extract thereof an effective amount to or by the subject.

The present invention also provides a method for inhibiting melanin production in a subject administration or ingestion of haguro-so or an organic solvent extract thereof of an effective amount to or by the subject.

The present invention also provides a method for whitening the skin in a subject comprising administration or ingestion of haguro-so or an organic solvent extract thereof of an effective amount to or by the subject.

Alternatively, the present invention provides a method for inhibiting a dopa oxidase activity in a subject comprising administration or ingestion of a compound represented by the above formula (I) (wherein $R_1$ to $R_9$ are as defined above) or a salt thereof of an effective amount to or by the subject.

The present invention also provides a method for inhibiting melanin production in a subject comprising administration or ingestion of a compound represented by the above formula (I) (wherein $R_1$ to $R_9$ are as defined above) or a salt thereof of an effective amount to or by the subject.

The present invention also provides a method for whitening the skin in a subject comprising administration or ingestion of a compound represented by the above formula (I) (wherein $R_1$ to $R_9$ are as defined above) or a salt thereof of an effective amount to or by the subject.

DETAILED DESCRIPTION OF THE INVENTION

Figure 1:
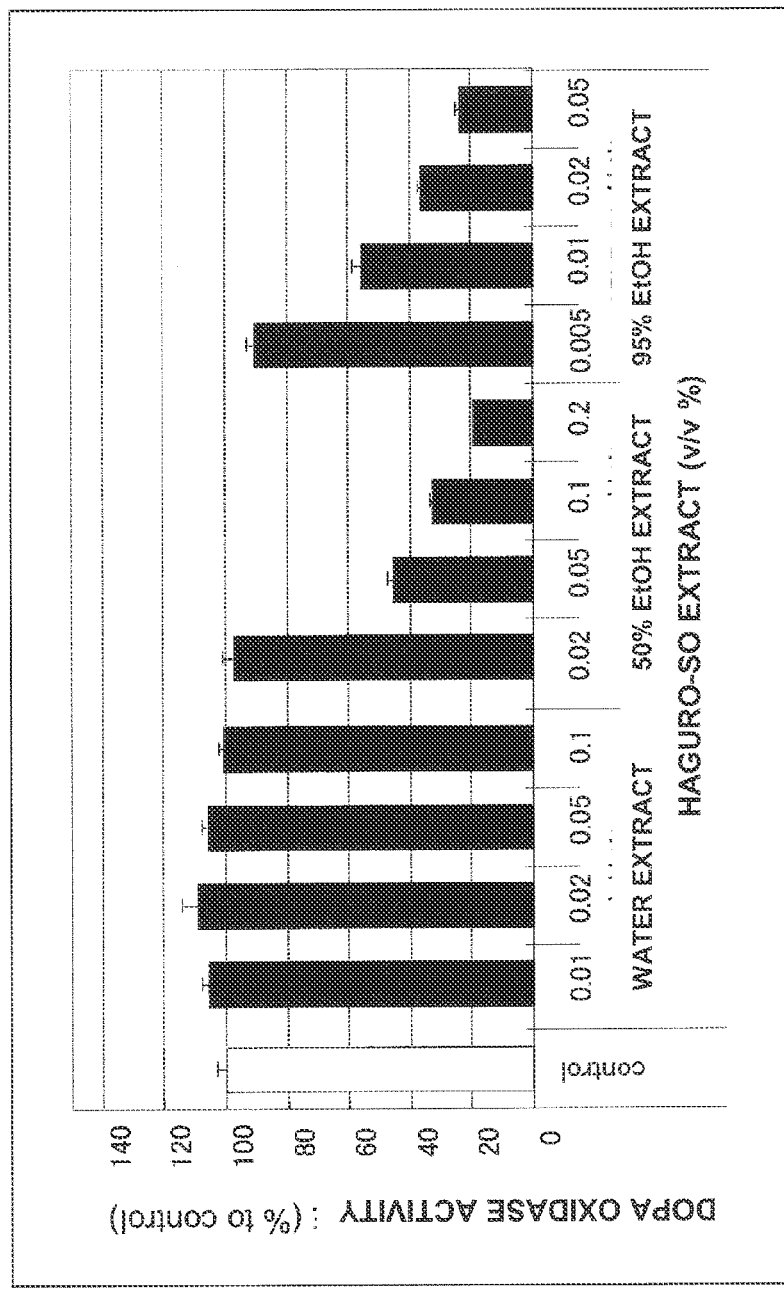
FIG. 1 shows the dopa oxidase activity inhibition by the haguro-so extracts. Error bar=±S.D.

The present invention relates to the provision of a skin whitening agent, a melanin production inhibitor, and a dopa oxidase activity inhibitor which are very safe, inhibit the dopa oxidase activity and are useful to be a cosmetic product, drug, or the like.

The present inventors searched for a substance having skin whitening effect, melanin production inhibitory effect, or the like, and found that haguro-so has dopa oxidase activity inhibitory effect and skin whitening effect. The present inventors further found that the active ingredient exhibiting the skin whitening effect in the above haguro-so is arylnaphthalene lignans having a specific structure, and that the arylnaphthalene lignans have a dopa oxidase activity inhibitory effect; therefore, haguro-so and the above mentioned ingredient are useful materials to be a drug, cosmetic product, external agent for the skin, skin whitening composition, or the like, which are effective in preventing, ameliorating, treating, or the like, the skin browning, speckles, freckles, or the like, associated with the melanin overproduction.

When the dopa oxidase activity inhibitor, the melanin production inhibitor, the skin whitening agent, or the external agent for the skin of the present invention is used, the melanin overproduction in the skin is inhibited, thereby preventing, ameliorating, or treating pigmentation such as suntan, speckles, or freckles.

In the present specification, the term "nontherapeutic" refers to the concept which excludes medical practice, that is, treatments to human body by a medical therapy.

In the present invention, the term "amelioration" means to turn a disease, symptoms, or conditions for the better, to prevent or delay a disease, symptoms, or conditions from exacerbating; or to reverse, prevent, or delay a disease, symptoms, or conditions from progressing.

In the present invention, the term "prevention" means to prevent or delay a disease or symptoms in an individual from developing; or to reduce the risk of incidence of a disease or symptoms in an individual.

Haguro-so in the present invention means *Peristrophe japonica* belonging to the Family Acanthaceae, Genus *Peristrophe*.

Haguro-so is used per se or by cutting, crushing, grinding, or squeezing the entire plant, leaves (leaf blade, petiole, or the like), fruit (ripe, unripe, or the like), seed, flower (petal, ovary, etc.), stem, rhizome, root, tuberous root, or the like, or by drying or powdering the processed products thereof. Preferred part to be used is the entire plant.

The extract of haguro-so may be any extract from the above parts unless otherwise specified, but the extract from the entire plant is preferred. The extract may be those directly extracted from the plant parts described above, but may also be those extracted after any part of the plant is cut, crushed, ground or squeezed and/or dried or powdered.

The extractant used for preparing a haguro-so extract is preferably an organic solvent, and may be a polar organic solvent or nonpolar organic solvent.

Examples of the organic solvent include monovalent, bivalent or polyvalent alcohols; ketones such as acetone and methyl ethyl ketone; esters such as methyl acetate and ethyl acetate; linear or cyclic ethers such as tetrahydrofuran and diethyl ether; polyethers such as polyethylene glycol; saturated or unsaturated hydrocarbons; aromatic hydrocarbons such as benzene and toluene; halogenated hydrocarbons such as dichloromethane, chloroform, dichloroethane, and carbon tetrachloride; pyridines; dimethyl sulfoxides; acetonitrile; carbon dioxide, supercritical carbon dioxide; and a fat or oil, waxes, other oils and the like; of these, alcohols and saturated carbon hydrocarbons are preferred in light of pharmacological activities.

The above alcohols are not particularly limited and examples include monovalent alcohols such as methanol, ethanol, propanol, butanol, amyl alcohol, hexanol, heptanol, and octanol; bivalent alcohols such as 1,3-butylene glycol, ethylene glycol, propylene glycol, 1,4-butanediol, 1,5-pentanediol, and 1,6-hexanediol; trivalent or higher alcohols such as glycerol and the like; of these monovalent alcohols and bivalent alcohols are preferred in light of pharmacological activities.

The above alcohols preferably have from 1 to 10, more preferably from 1 to 4 carbon atoms. Specific examples include methanol, ethanol, 1,3-butylene glycol, n-propanol, isopropanol, n-butanol, isobutanol, sec-butanol, t-butanol and the like; and ethanol and 1,3-butylene glycol are preferred due to easy managebility.

The saturated hydrocarbons may be linear, branched, or cyclic saturated hydrocarbons, and examples include linear saturated hydrocarbons such as methane, ethane, propane, n-butane, n-pentane, n-hexane, n-heptane, n-octane, n-nonane, and n-decane; branched saturated hydrocarbons such as 2-methylbutane, 2,2-dimethylpropane, 2-methylpentane, 3-methylpentane, 2,2-dimethylbutane, 2,3-dimethylbutane, 2-methylhexane, 3-methylhexane, and 2,2,4-trimethylpentane; cyclic saturated hydrocarbons such as cyclopentane, cyclohexane, and cycloheptane and the like; of these linear saturated hydrocarbons are preferred in light of pharmacological activities.

The above saturated hydrocarbons preferably have from 1 to 10, more preferably from 5 to 10, even more preferably from 5 to 8 carbon atoms. Specific examples include n-pentane, n-hexane, n-heptane, n-octane, 2-methylbutane, 2,2-dimethylpropane, 2-methylpentane, 3-methylpentane, 2,2-dimethylbutane, 2,3-dimethylbutane, 2-methylhexane, 3-methylhexane, cyclohexane and the like; and n-hexane is preferred due to easy manageability.

The above organic solvent may be used singly, or two or more may be used as a mixed solvent.

The organic solvent used in the present invention may be an aqueous organic solvent.

The organic solvent to be used as the above aqueous organic solvent is preferably a hydrophilic organic solvent.

The hydrophilic organic solvent herein is not particularly limited, but examples include a protonic hydrophilic organic solvent such as alcohols, acetic acid, or pyridines, described above, and an aprotic hydrophilic organic solvent such as ketones, acetonitrile, or dimethylsulfoxide; of these, a protonic hydrophilic organic solvent is preferred. The protonic hydrophilic organic solvent is, due to easy manageability preferably the above alcohols, more preferably the above monovalent and bivalent alcohols, even more preferably $C_{1-4}$ alcohols, even more preferably ethanol and 1,3-butylene glycol.

These may be used singly, or two or more may be used as a mixed solvent.

The water content in the above aqueous organic solvent is not particularly limited, but may be, in light of pharmacological activities, 70% by volume or less, preferably 50% by volume or less, more preferably 25% by volume or less.

For example, it is preferable, in light of pharmacological activities, that the hydrophilic organic solvent concentration in the aqueous organic solvent be 30% by volume or more, more preferably from 50 to 100% by volume, even more preferably from 75 to 100% by volume, even more preferably from 75 to 99.9% by volume.

The extraction technique in the present invention is not particularly limited, and examples include liquid-liquid extraction, solid-liquid extraction, immersion, infusion, decoction, reflux extraction, ultrasonic extraction, microwave extraction, and centrifugal extraction; and they may be used singly or in combinations of two or more. At this time, a batch type extractor, Soxhlet extractor, or the like, may be used.

The extraction conditions are not particularly limited, but the extraction temperature is preferably from 0 to 100° C., more preferably from 4 to 80° C., even more preferably from 4 to 40° C., and the extraction period is preferably from 1 minute to 50 days, more preferably from 1 hour to 50 days, even more preferably from 1 to 30 days.

The amount of the solvent used is preferably from 1 to 100 parts by mass, more preferably from 1 to 50 parts by mass, even more preferably from 5 to 40 parts by mass, per part by mass of the plant (on a dried product basis).

The extraction, as an example, is preferably carried out using from 1 to 50 parts by mass of a monovalent or bivalent alcohol aqueous solution (preferably $C_{1-3}$ monovalent alcohols or $C_{3-5}$ bivalent alcohols) comprising 50 to 95% by volume of the above solvent and/or saturated hydrocarbons (preferably $C_{5-10}$ saturated hydrocarbons) per part by mass of a plant (on a dried product basis) at from 10 to 40° C. (preferably from 20 to 40° C.) for from 1 hour to 30 days (preferably from 5 to 20 days).

Alternatively, the extraction may be carried out in a non-oxidizing atmosphere while removing the dissolved oxygen by boiling deaeration or passing through an inert gas such as nitrogen gas.

The haguro-so extract obtained as described above may be used per se, but may be used as further diluted, concentrated, or freeze-dried, and/or prepared to be a liquid, powder, or paste.

Additionally, after haguro-so is extracted with the above solvent, preferably the above hydrophilic organic solvent, an extraction technique such as water washing, liquid-liquid separation, or liquid-solid extraction, may be used because they can remove water-soluble impurities, which is advantageous in light of pharmacological activities.

Specifically, a solvent such as water and/or a hydrophobic organic solvent, is added to the haguro-so extract, preferably a hydrophilic organic solvent extract, and a physical technique such as mixing, stirring, shaking, or centrifuging is subsequently carried out to recover a fraction (layer) mainly containing pharmacologically active ingredients. This procedure may suitably be repeated 1 to 3 times. After recovery, the fraction may be concentrated and the obtained solid product may be dissolved in an alcohol aqueous solution or the like.

The solvent to be added to the above organic solvent extract (hereinafter referred to as an "additive solvent") may be water, a hydrophobic organic solvent, or a water-hydrophobic organic solvent mixture.

The hydrophobic organic solvent herein is not particularly limited, but examples include saturated or unsaturated hydrocarbons; aromatic hydrocarbons; halogenated hydrocarbons; linear or cyclic ethers or polyethers; oils and the like, as mentioned earlier. Of these, saturated or unsaturated hydrocarbons are preferable in light of pharmacological activities, with saturated hydrocarbons being more preferable. Of the saturated hydrocarbons, $C_{5-10}$ saturated hydrocarbons are preferable, $C_{5-8}$ linear or branched saturated hydrocarbons are more preferable, with n-hexane being even more preferable.

These hydrophobic organic solvents may be used singly, or two or more may be mixed and used.

The water-hydrophobic organic solvent mixture when used as the above additive solvent is advantageous because, water wash and the hydrophobic organic solvent extraction can be carried out simultaneously, thereby being efficient in work performance. Water and a hydrophobic organic solvent may be added together or separately to the solvent extract described above.

When the extraction, particularly a liquid-liquid separation (distribution), is carrier out using the water-hydrophobic organic solvent mixture, alcohols, inorganic salts, or the like, may further be added for the purpose of improving the layer separation properties or removing acidic ingredients and basic ingredients mixed in the extract.

The mixing ratio of water to the hydrophobic organic solvent in the above water-hydrophobic organic solvent mixture is not particularly limited, but is preferably water (v):hydrophobic organic solvent (v)=from 1:0.1 to 1:10, more preferably from 1:0.1 to 1:5.

The above alcohols may be added to the above additive solvent to easily remove the water-soluble impurities, but, in this instance, it is preferable that the content of alcohols in the solvent be from 1 to 50% by volume.

Water-soluble inorganic salts may suitably be added to the above additive solvent to easily remove the water-soluble impurities, and examples of the water-soluble inorganic salt include chlorides such as sodium chloride, and potassium chloride; carbonates such as sodium carbonate; hydrogen carbonates such as sodium hydrogencarbonate; sulfates such as sodium sulfate; phosphates such as sodium phosphate; and the like.

The content of water-soluble inorganic salt in water is preferably from 0.5 to 10% (m/v).

The amount of additive solvent to be used is not particularly limited but is preferably from 10 to 100 mL to 1 g of the dried solid product. The extraction temperature is preferably from 4 to 80° C., more preferably from 10 to 40° C., even more preferably from 10 to 30° C.

The haguro-so organic solvent extract obtained as described above may be used per se, but may be used as diluted, concentrated, or freeze-dried, and/or prepared to be a liquid, powder, or paste.

Additionally, if necessary, the haguro-so organic solvent extract may be subjected to a separation refining technique such as activated carbon treatment, liquid chromatography, liquid-liquid distribution, gel filtration, or precision distillation, to remove inert impurities and the like, for further refinement.

The present inventors also found a compound represented by the following formula (I) (hereinafter also referred to as the formula (I) compound) based on the structure of the active ingredients contained in the haguro-so extract prepared by the above procedure.

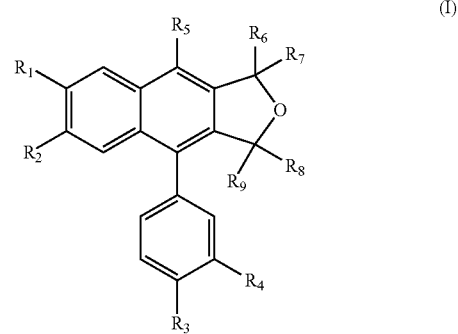

(I)

In the formula (I), $R_1$ and $R_2$, being the same or different, each represent a hydroxyl group, or a $C_{1-4}$ linear or branched alkoxy group, or $R_1$ and $R_2$ together form a methylenedioxy group. $R_3$ and $R_4$, being the same or different, each represent a hydroxyl group, or a $C_{1-4}$ linear or branched alkoxy group, or $R_3$ and $R_4$ together form a methylenedioxy group. $R_1$ and $R_2$, and $R_3$ and $R_4$ herein may both form a methylenedioxy group simultaneously, but only either $R_1$ and $R_2$, or $R_3$ and $R_4$ preferably form a methylenedioxy group.

Preferably, $R_1$ and $R_2$ are both a $C_{1-4}$ linear or branched alkoxy group and $R_3$ and $R_4$ together form a methylenedioxy group, or $R_1$ and $R_2$ together form a methylenedioxy group and $R_3$ and $R_4$ are both a $C_{1-4}$ linear or branched alkoxy group. More preferably, $R_1$ and $R_2$ are both a $C_{1-4}$ linear or branched alkoxy group, and $R_3$ and $R_4$ together form a methylenedioxy group.

Examples of the $C_{1-4}$ linear or branched alkoxy group represented by $R_1$ to $R_4$ include methoxy, ethoxy, n-propoxy, iso-propoxy, n-butoxy, tert-butoxy, sec-butoxy, and iso-butoxy. Of these, methoxy and ethoxy are preferable, with methoxy being more preferable.

In the formula (I), $R_5$ represents a hydrogen atom, a hydroxyl group, a $C_{1-5}$ linear or branched alkoxy group, a $C_{1-4}$ acyl group, or a sugar residue.

Examples of the $C_{1-5}$ linear or branched alkoxy group include methoxy, ethoxy, propoxy, isopropoxy, butoxy, pentyloxy, ethoxymethyl, ethoxyethyl, propoxymethyl, propoxyethyl, and butoxymethyl; of these, methoxy, ethoxy, propoxy, isopropoxy, and butoxy are preferable, with methoxy and ethoxy being more preferable.

Examples of the $C_{1-4}$ acyl group include formyloxy, acetyloxy, propionyloxy, and butyryloxy; of these, acetyloxy and propionyloxy are preferable, with acetyloxy being more preferable.

Examples of the sugar residue include (D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy and (3-O-methyl-β-D-glucopyranosyl)oxy; of these, (D-apio-β-D-furanosyl)oxy is preferable.

In the formula (I), $R_6$ and $R_7$ are both a hydrogen atom, and $R_8$ and $R_9$ together represent an oxygen atom. Alternatively, $R_5$ and $R_7$ together represent an oxygen atom, and $R_8$ and $R_9$ are both a hydrogen atom. Preferably, $R_6$ and $R_7$ are both a hydrogen atom, and $R_8$ and $R_9$ together represent an oxygen atom.

Preferable examples of the formula (I) compound include the following.
Justicidin A(4,6,7-trimethoxy-9-(1,3-benzodioxol-5-yl) naphtho[2,3-c]furan-1(3H)-one)
Justicidin B(6,7-dimethoxy-9-(1,3-benzodioxol-5-yl)naphtho[2,3-c]furan-1(3H)-one)
Justicidin C(4-(1,3-benzodioxol-5-yl)-6,7,9-trimethoxynaphtho[2,3-c]furan-1(3H)-one)
Retrojusticidin B(6,7-dimethoxy-4-(1,3-benzodioxol-5-yl) naphtho[2,3-c]furan-1(3H)-one)
Justicidin E(4-(1,3-benzodioxol-5-yl)-6,7-methylene dioxynaphtho[2,3-c]furan-1(3H)-one)
Tuberculatin((−)-4-[(D-apio-β-D-furanosyl)oxy]-9-(1,3-benzodioxol-5-yl)-6,7-dimethoxy-1H-naphtho[2,3-c]furan-3-one)
Diphyllin(4-hydroxy-6,7-dimethoxy-9-(1,3-benzodioxol-5-yl)naphtho[2,3-c]furan-1(3H)-one)
Diphyllin apioside(9-(1,3-benzodioxol-5-yl)-4-(D-apio-β-D-furanosyloxy)-6,7-dimethoxynaphtho[2,3-c]furan-1(3H)-one)
Haplomyrtoside(9-(1,3-benzodioxol-5-yl)-7-hydroxy-6-methoxy-4-(D-apio-β-D-furanosyloxy)naphtho[2,3-c]furan-1(3H)-one)
Haplomyrtin(9-(1,3-benzodioxol-5-yl)-4,7-dihydroxy-6-methoxynaphtho[2,3-c]furan-1(3H)-one)
Cleistanthin A(9-(1,3-benzodioxol-5-yl)-4-[(3-O,4-O-dimethyl-D-xylopyranosyl)oxy]-6,7-dimethoxynaphtho[2,3-c]furan-1(3H)-one)
Cleistanthin B(9-(1,3-benzodioxol-5-yl)-4-(β-D-glucopyranosyloxy)-6,7-dimethoxynaphtho[2,3-c]furan-1(3H)-one)
Cleistanthin D(4-(2-O,3-O,4-O-trimethyl-β-D-xylopyranosyloxy)-6,7-dimethoxy-9-(1,3-benzodioxol-5-yl)-1,3-dihydronaphtho[2,3-c]furan-1-one)
Daurinol(9-(1,3-benzodioxol-5-yl)-6-hydroxy-7-methoxynaphtho[2,3-c]furan-1(3H)-one)
Isodaurinol(9-(1,3-benzodioxol-5-yl)-7-hydroxy-6-methoxynaphtho[2,3-c]furan-1(3H)-one)
Collinusin((+)-9-(1,3-benzodioxol-5-yl)-3a,4-dihydro-6,7-dimethoxynaphtho[2,3-c]furan-1(3H)-one)
Taiwanin C(5-(1,3-benzodioxol-5-yl)furo[3',4':6,7]naphtho[2,3-d]-1,3-dioxol-6(8H)-one)
Taiwanin E(5-(1,3-benzodioxol-5-yl)-9-hydroxyfuro[3',4':6,7]naphtho[2,3-d]-1,3-dioxol-6(8H)-one)
Phyllanthusmin A(4,6-dimethoxy-7-hydroxy-9-(1,3-benzodioxol-5-yl)-1,3-dihydronaphtho[2,3-c]furan-1-one)
Justicidin F(5-(1,3-benzodioxol-5-yl)-9-methoxyfuro[3',4':6,7]naphtho[2,3-d]-1,3-dioxol-6(8H)-one)
4-ethoxy-6,7-dimethoxy-9-(1,3-benzodioxol-5-yl)naphtho[2,3-c]furan-1(3H)-one
4-acetoxy-6,7-dimethoxy-9-(1,3-benzodioxol-5-yl)naphtho[2,3-c]furan-1(3H)-one
(3aR)-3a,4-dihydro-6,7-dimethoxy-9-(1,3-benzodioxol-5-yl)naphtho[2,3-c]furan-1(3H)-one
(3aS)-3a,4-dihydro-6,7-dimethoxy-9-(1,3-benzodioxol-5-yl)naphtho[2,3-c]furan-1(3H)-one
4-(3-O-methyl-β-D-glucopyranosyloxy)-6,7-dimethoxy-9-(1,3-benzodioxol-5-yl)naphtho[2,3-c]furan-1(3H)-one Of the compounds mentioned above, more preferable examples include justicidin A, justicidin B, tuberculatin, diphyllin, 4-ethoxy-6,7-dimethoxy-9-(1,3-benzodioxol-5-yl)naphtho[2,3-c]furan-1(3H)-one, 4-acetoxy-6,7-dimethoxy-9-(1,3-benzodioxol-5-yl)naphtho[2,3-c]furan-1(3H)-one, and justicidin F.

Glycosides of the justicidins mentioned above are also included as preferable examples of the compound of the present invention.

The above formula (I) compound may be synthesized in accordance with a know method, or a commercial product may be purchased. The synthesis can be carried out in accordance with the method described in, for example, J. Org. Chem., 1996, 61: 3452-3457. A part of the synthesis method is described below.

Synthesis of Diphyllin

An acetal compound obtained by the reaction of 2-bromo-5,6-dimethoxybenzaldehyde and ethylene glycol is reacted with 3,4-(methylenedioxy)benzaldehyde under a basic condition, further reacted with DEADC under an elevated temperature condition, finally followed by reduction by $NaBH_4$, thereby obtaining an intended compound.

Synthesis of Justicidin B

An acetal compound obtained by the reaction of 2-bromo-5,6-dimethoxybenzaldehyde and ethylene glycol is reacted with 3,4-(methylenedioxy)benzaldehyde under a basic condition, heated with maleic anhydride under an acidic condition, finally followed by reduction by $NaBH_4$, thereby obtaining an intended compound.

Synthesis of Justicidin A

An intended compound may be obtained by the reaction of methyl iodide with diphyllin under a basic condition.

Alternatively, in accordance with the method described in Med. Chem. Res., 2010, 19: 71-76, bromoalkane is added to diphyllin under a basic condition to obtain 4-etoxy-6,7-dimethoxy-9-(1,3-benzodioxol-5-yl)naphtho[2,3-c]furan-1(3H)-one.

Alternatively, 4-acetoxy-6,7-dimethoxy-9-(1,3-benzodioxol-5-yl)naphtho[2,3-c]furan-1(3H)-one can be obtained by, using diphyllin as a starting substance, acylating a hydroxy group of the diphyllin by a typical acylation method, as described in the Fifth Series of Experimental Chemistry 16 ("jikken kagaku kouza 16" in Japanese), p. 42.

Examples of the commercial product include Catalog No. ST077116 of TimTec Inc.; Catalog No. P2000N-07371, P2000N-22338, P2000N-10719 of Pharmeks LTD.; and Catalog No. ABS-00020012-001 of ChromaDex Inc.

Alternatively, the formula (I) compound can be isolated from plants such as haguro-so, (*Peristrophe japonica*), kitsunenomago (*Justicia procumbens*), *Haplophyllum patavinum*, or *Cleistanthus Collinus*.

The isolation from *Haplophyllum patavinum* and *Cleistanthus Collinus* may be carried out in accordance with the method described in Chem. Pharm. Bull., 2002, 50: 844-846 and Tetrahedron, 1969, 25: 2815-2821, and examples of the compound isolated from these plants include justicidin B, diphyllin, and cleistanthin A.

When isolated from haguro-so and kitsunenomago, the extract of these plants is refined by column chromatography or the like, to obtain the formula (I) compound. Examples of the compound isolated from these plants include justicidin A, justicidin B, and tuberculatin.

More specifically, any part of haguro-so or kitsunenomago, preferably the entire plant when haguro-so is used or the entire plant when kitsunenomago is used, is dried and crushed as necessary and extracted, and the obtained extract is concentrated as necessary and impurities are removed therefrom, followed by column chromatography refining.

The haguro-so or kitsunenomago extract is preferably prepared in accordance with, for example, the preparation procedure of a haguro-so extract described above. More specifically, the solvent used for the extraction is preferably an organic solvent such as polar organic solvents or nonpolar organic solvents. Examples of the organic solvent include monovalent, bivalent, or polyvalent alcohols; ketones such as acetone and methyl ethyl ketone; esters such as methyl acetate and ethyl acetate; linear or cyclic ethers such as tetrahydrofuran and diethyl ether; polyethers such as polyethylene glycol; saturated or unsaturated hydrocarbons; aromatic hydrocarbons such as benzene and toluene; halogenated hydrocarbons such as dichloromethane, chloroform, dichloroethane, and carbon tetrachloride; pyridines; dimethyl sulfoxides; acetonitrile; carbon dioxide, supercritical carbon dioxide; a fat or oil, waxes, other oils and the like. These organic solvents may be used singly, or two or more may be mixed and used.

The above alcohols are not particularly limited, but preferable examples include methanol, ethanol, 1,3-butylene glycol, n-propanol, isopropanol, n-butanol, isobutanol, sec-butanol, and t-butanol; with ethanol and 1,3-butylene glycol being more preferable due to easy manageability.

The saturated hydrocarbons may be linear, branched, or cyclic saturated hydrocarbons, and preferable examples include n-pentane, n-hexane, n-heptane, n-octane, 2-methylbutane, 2,2-dimethylpropane, 2-methylpentane, 3-methylpentane, 2,2-dimethylbutane, 2,3-dimethylbutane, 2-methylhexane, 3-methylhexane, and cyclohexane; with n-hexane being preferable due to easy manageability.

The organic solvent used in the extraction may be an aqueous organic solvent. The organic solvent to be used as the above aqueous organic solvent is not particularly limited, but preferable examples include the above alcohols, with ethanol and 1,3-butylene glycol being more preferable. The organic solvent concentration in the aqueous organic solvent is 30% by volume or more, more preferably from 50 to 100% by volume, even more preferably from 75 to 100% by volume, even more preferably from 75 to 99.9% by volume.

The extraction technique is not particularly limited, and examples include liquid-liquid extraction, solid-liquid extraction, immersion, infusion, decoction, reflux extraction, ultrasonic extraction, microwave extraction, centrifugal extraction and the like, and they may be used singly or in combinations of two or more. At this time, a batch type extractor, Soxhlet extractor, or the like, may be used. Alternatively, the extraction may be carried out in a nonoxidizing atmosphere while removing the dissolved oxygen by boiling deaeration or passing through an inert gas such as nitrogen gas.

An example of the extraction is a condition using 1 to 50 parts by mass of a monovalent or bivalent alcohol aqueous solution comprising from 50 to 95% by volume of a solvent as the extractant per part by mass of a plant (on a dried product basis) at from 10 to 40° C., preferably from 20 to 40° C., for from 1 hour to 30 days, preferably from 5 to 20 days.

The haguro-so or kitsunenomago extract obtained as above is preferably concentrated and solidified to dryness as necessary and subsequently subjected to water wash, liquid-liquid distribution, solid-liquid extraction, or the like, before applied to the column chromatography. Using these techniques can remove water-soluble impurities, and the like, from the extract, hence advantageous.

Specifically, a solvent such as water and/or a hydrophobic organic solvent, is added to the haguro-so or kitsunenomago extract, preferably a hydrophilic organic solvent extract, and a physical technique such as mixing, stirring, shaking, or centrifuging, is subsequently carried out to recover a hydrophobic fraction (layer) mainly containing active ingredients. This procedure may suitably be repeated 1 to 3 times. The collected hydrophobic fraction is subsequently subjected to the column chromatography.

The solvent to be added to the above extract (hereinafter referred to as an "additive solvent") may be water, a hydrophobic organic solvent, or a water-hydrophobic organic solvent mixture, but a water-hydrophobic organic solvent mixture when used is advantageous because water wash and a hydrophobic organic solvent extraction can be carried out simultaneously, thereby being efficient in work performance. The hydrophobic organic solvent herein is not particularly limited, but examples include saturated or unsaturated hydrocarbons; aromatic hydrocarbons; halogenated hydrocarbons; linear or cyclic ethers or polyethers; esters such as ethyl acetate; oils; and the like as mentioned above; of these, n-hexane, ethyl acetate, and the like, are preferable. These hydrophobic organic solvents may be used singly, or two or more may be mixed and used.

The mixing ratio of water to a hydrophobic organic solvent in the above water-hydrophobic organic solvent mixture is not particularly limited, but is preferably water (v):hydrophobic organic solvent (v)=from 1:0.1 to 1:10, more preferably from 1:0.1 to 1:5.

The amount of additive solvent to be used is not particularly limited, but is preferably from 10 to 100 mL to 1 g of a dried solid product of the extract. The temperature is preferably from 4 to 80° C., more preferably from 10 to 40° C., even more preferably from 10 to 30° C.

An example of the liquid-liquid distribution by the additive solvent is a liquid-liquid distribution by a water-ethyl acetate (1:1) solvent of an extract from which the solvent is removed by concentration. The obtained ethyl acetate layer is subjected to the column chromatography described below.

The haguro-so or kitsunenomago extract obtained by the above procedure, or the extract subjected, as necessary, to a further extraction using the above additive solvent or liquid-liquid distribution, is subjected to column chromatography such as silica gel column.

In the column chromatography, for example, the extract was eluted with a hexane-ethyl acetate gradient ramping from a 0% to 100% ethyl acetate ratio over 60 minutes, subsequently with an ethyl acetate-methanol gradient ramping from a 0% to 10% methanol ratio over 30 minutes, and with 100% methanol over 30 minutes, whereby the fractions eluted at from about a hexane/ethyl acetate=1/9 ratio to 100% MeOH are collected. These fractions can be separated into those insoluble and those soluble in MeOH. The MeOH-insoluble fraction is subjected to the reversed phase HPLC in a double-layer system consisting of 0.1% formic acid aqueous solution-acetonitrile and eluted with 50% acetonitrile over 20 minutes, whereby the fractions eluted between about 10 and 15 minutes may be collected. On the other hand, the MeOH-soluble fraction is subjected to the reversed phase HPLC in a double-layer system consisting of 0.1% formic acid aqueous solution-acetonitrile and eluted with the 35% acetonitrile over 16 minutes, whereby the fractions eluted between about 12 and 15 minutes may be collected.

The dopa oxidase activity of the obtained fractions are measured as necessary to confirm that the intended formula (I) compound is contained therein. The method for measuring the dopa oxidase activity may be carried out in accordance with the method described, for example, in Examples to be described later.

As described later in Examples, the haguro-so organic solvent extract and the above formula (I) compound have outstanding dopa oxidase activity inhibitory effects, which intensely inhibit the dopa oxidase activity. The dopa oxidase activity is deeply associated with the melanin production mechanism (Non Patent Document 1) and for this reason, when the dopa oxidase activity is inhibited, the melanin production inhibitory effects, skin whitening effects, effects for preventing, ameliorating, or treating symptoms of skin pigmentation, speckles, and freckles, caused by the skin exposure to ultraviolet rays or the like, can be obtained. The melanin production inhibitory effects rendered by the haguro-so extract or the formula (I) compound in the skin tissues are demonstrated in Examples to be described later. The haguro-so extract and the formula (I) compound also have low cytotoxicity, and hence can be used safely for an extended period of time.

More specifically, the haguro-so extract or organic solvent extract thereof, or the formula (I) compound or a salt thereof, can be used to inhibit the dopa oxidase activity, inhibit the melanin production, whiten the skin, or prevent, ameliorate, or treat symptoms such as skin pigmentation, speckles, or freckles; or can be used as an external agent for the skin which exhibits any of these effects.

Consequently, in an aspect, the present invention provides a dopa oxidase activity inhibitor comprising the formula (I) compound or a salt thereof as an active ingredient. The present invention also provides a melanin production inhibitor comprising the formula (I) compound or a salt thereof as an active ingredient. The present invention also provides a skin whitening agent comprising the formula (I) compound or a salt thereof as an active ingredient.

In another aspect, the present invention provides a dopa oxidase activity inhibitor comprising haguro-so or an organic solvent extract thereof as an active ingredient. The present invention also provides a melanin production inhibitor comprising haguro-so or an organic solvent extract thereof as an active ingredient. The present invention also provides a skin whitening agent comprising haguro-so or an organic solvent extract thereof as an active ingredient. The present invention also provides an external agent for the skin comprising haguro-so or an organic solvent extract thereof as an active ingredient.

These uses are applicable to a human or a non-human animal, or tissues, organs, or cells derived therefrom, and may be therapeutic or non-therapeutic.

Accordingly, in an aspect, the present invention provides use of the formula (I) compound or a salt thereof for dopa oxidase activity inhibition. The present invention also provides use of the formula (I) compound or a salt thereof for melanin production inhibition. The present invention also provides use of the formula (I) compound or a salt thereof for skin whitening.

In another aspect, the present invention further provides use of haguro-so or an organic solvent extract thereof for dopa oxidase activity inhibition. The present invention also provides use of haguro-so or an organic solvent extract thereof for melanin production inhibition. The present invention also provides use of haguro-so or an organic solvent extract thereof for skin whitening. The present invention also provides use of haguro-so or an organic solvent extract thereof for the external skin.

These uses are applicable to a human or a non-human animal, or tissues, organs, or cells derived therefrom, and may be therapeutic or non-therapeutic.

In still another aspect, the present invention provides the formula (I) compound or a salt thereof for use in dopa oxidase activity inhibition. The present invention also provides the formula (I) compound or a salt thereof for use in melanin production inhibition. The present invention also provides the formula (I) compound or a salt thereof for use in skin whitening.

In another aspect, the present invention provides haguro-so or an organic solvent extract thereof for use in dopa oxidase activity inhibition. The present invention also provides haguro-so or an organic solvent extract thereof for use in melanin production inhibition. The present invention also provides haguro-so or an organic solvent extract thereof for use in skin whitening. The present invention also provides haguro-so or an organic solvent extract thereof for use in the external skin.

These uses are applicable to a human or a non-human animal, or tissues, organs, or cells derived therefrom, and may be therapeutic or non-therapeutic.

In another aspect, the present invention provides use of the formula (I) compound or a salt thereof for producing a dopa oxidase activity inhibitor. The present invention also provides use of the formula (I) compound or a salt thereof for producing a melanin production inhibitor. The present invention also provides use of the formula (I) compound or a salt thereof for producing a skin whitening agent.

In another aspect, the present invention provides use of haguro-so or an organic solvent extract thereof for producing a dopa oxidase activity inhibitor. The present invention also provides use of haguro-so or an organic solvent extract thereof for producing a melanin production inhibitor. The present invention also provides use of haguro-so or an organic solvent extract thereof for producing a skin whitening agent. The present invention also provides use of haguro-so or an organic solvent extract thereof for producing an external agent for the skin.

In an aspect, the melanin production inhibitory effect or the skin whitening effect by the above agent is rendered by the dopa oxidase activity inhibitory effect.

In another aspect, the dopa oxidase activity inhibitor, the melanin production inhibitor, and the skin whitening agent can be in the form of an external agent for the skin.

According to the present invention, for example, the above haguro-so or an extract thereof, or the formula (I) compound or a salt thereof, can be added as a material to compositions, drugs, quasi drugs, external agents, cosmetic products, drink or food products, feeds, or raw materials for drink or food products or feeds for inhibiting the dopa oxidase activity, inhibiting the melanin production, whitening the skin, or preventing, ameliorating, or treating symptoms such as skin pigmentation, speckles, or freckles; or can be used for producing these products. These compositions, drugs, quasi drugs, external agents, cosmetic products, drink or food products, feeds, and raw materials for drink or food products or feeds, and the like, are also encompassed within the scope of the present invention.

The above compositions, drugs, quasi drugs, external agents, cosmetic products, drink or food products, feeds, or raw materials for drink or food products or feeds can be produced or used for human or non-human animal. The above Haguro-so or an extract thereof, or the formula (I) compound or a salt thereof, is added to the compositions, drugs, quasi drugs, external agents, cosmetic products, drink or food products, feeds, or raw materials for drink or food products or feeds, and can be the active ingredient for inhibiting the dopa oxidase activity, inhibiting the melanin production, whitening the skin, or preventing, ameliorating, or treating symptoms such as skin pigmentation, speckles, or freckles.

The drugs or quasi drugs comprise the above haguro-so or an extract thereof, or the formula (I) compound or a salt thereof, as the active ingredient. The drugs or quasi drugs can be administered in any administration form. The administration may be oral or parenteral. Examples of the dosage form for oral administration include solid administration forms such as tablets, coated tablets, granules, powders, and capsules, and liquid administration forms such as elixirs, syrups and suspensions; examples of the dosage form for parenteral administration include injections, infusions, topicals, external agents, subcutaneous, transmucosal, transnasal, enteric, inhalation, suppositories, bolus, and patches.

The drugs or quasi drugs can be preferably in the form of an external agent for the skin.

The drugs or quasi drugs may comprise the above haguro-so or an extract thereof, or the formula (I) compound or a salt thereof, singly or in combination, or may comprise in combination with a pharmaceutically acceptable carrier. Examples of the carrier include an excipient, coating agent, binder, extender, disintegrator, lubricant, diluent, osmotic pressure regulator, pH regulator, dispersant, emulsifier, preservative, stabilizer, antioxidant, colorant, ultraviolet absorber, moisturizer, thickener, activity enhancer, anti-inflammatory agent, disinfecting agent, perfume, flavor, odor improver and the like. The drugs and quasi drugs may also comprise other active ingredients and pharmacological ingredients insofar as the dopa oxidase activity inhibitory effects of the above haguro-so or an extract thereof, or the formula (I) compound or a salt thereof, are not affected.

The cosmetic products comprise the above haguro-so or an extract thereof, or the formula (I) compound or a salt thereof as the active ingredient. The cosmetic products may comprise the above haguro-so or an extract thereof, or the formula (I) compound or a salt thereof singly or in combination, or may comprise in combination with a cosmetically acceptable carrier. Examples of the carrier include an excipient, coating agent, binder, extender, disintegrator, lubricant, diluent, osmotic pressure regulator, pH regulator, dispersant, emulsifier, preservative, stabilizer, antioxidant, colorant, ultraviolet absorber, moisturizer, thickener, activity enhancer, anti-inflammatory agent, disinfecting agent, perfume, flavor, odor improver and the like.

The cosmetic products may also comprise other active ingredients and cosmetic ingredients such as a moisturizer, skin whitening agent, UV protector, cell activator, cleaner, keratolytic agent, and make-up components (e.g., a makeup base, foundation, face finishing powder, powder, cheek color, rouge, eye makeup, eyebrow pencil, mascara, etc.) insofar as the dopa oxidase activity inhibitory effects of the above haguro-so or an extract thereof, or the formula (I) compound or a salt thereof, are not affected.

Examples of the cosmetic form include any form which can be used for a cosmetic product such as creams, emulsions, lotions, suspensions, gels, powders, packs, sheets, patches, sticks, and cake.

The cosmetic products are preferably a skin whitening cosmetic product, and also preferably an external cosmetic product for the skin. The cosmetic products are more preferably an external cosmetic product for skin whitening.

The above drugs, quasi drugs, or cosmetic products can be produced by a routine method from the above haguro-so, an extract thereof, or the formula (I) compound or a salt thereof, or in combination as necessary with the above carrier and/or other active ingredients, cosmetic ingredients, or pharmacological ingredients.

For example, the above-described external drug or quasi drug for the skin or external cosmetic product for the skin can be prepared from the above haguro-so or an extract thereof, or the formula (I) compound or a salt thereof singly, or in combination with those typically added to external agents, external pharmaceutical products, quasi drugs, or cosmetic products for the skin such as oils or oily substances (fats or oils, waxes, higher fatty acids, essential oils, silicone oils, or the like), moisturizers (glycerol, sorbitol, gelatin, polyethylene glycol, or the like), powders (chalks, talcs, Fuller's earth, kaolin, starch, rubber, or the like), dye, emulsifier, solubilizer, cleaner, ultraviolet absorber, thickener, medicinal component, perfume, resin, antibacterial and antifungal agent, other plant extracts (crude drugs, Kanpo products, herbs), alcohols, polyvalent alcohols, inorganic acids (bicarbonate, carbonate, sodium chloride, potassium chloride, sodium sulfate, or the like), organic acids (succinic acid, glutaric acid, fumaric acid, glutamic acid, malic acid, citric acid, ascorbic acid, or the like), vitamins (vitamin As, vitamin Es, vitamin Bs, vitamin C, folic acid, or the like), water-soluble polymers, anionic surfactants (alkylbenzene sulfonate, alkylsulfate, or the like), cationic surfactants (alkyl quaternary ammonium salt, alkyl dimethyl benzyl ammonium salt, or the like), nonionic surfactants (polyoxyethylene alkyl ether, polyoxyethylene alkyl phenyl ether, or the like), and amphoteric surfactants (imidazoline or carbobetaine containing an alkyl group, or the like).

The content of haguro-so or an extract thereof in the drug, quasi drug, or cosmetic product is, on a dry weight basis, preferably from 0.00001 to 20% by mass, more preferably from 0.0001 to 10% by mass, and, the content in the cosmetic product is, on a dry weight basis, preferably from 0.0001 to 20% by mass, more preferably from 0.0001 to 10% by mass. The content of the formula (I) compound or a salt thereof in the drug, quasi drug, or cosmetic product is, on a formula (I) compound basis, preferably from $1.0 \times 10^{-10}$ to 0.01% by mass, more preferably from $1.0 \times 10^{-8}$ to 0.005% by mass.

The above drink or food products and feeds are intended to function for inhibiting the dopa oxidase activity, inhibiting the melanin production, whitening the skin, or preventing, ameliorating, or treating symptoms such as skin pigmentation, speckles, or freckles; and can be food products, functional food products, food products for sick people, foods for specified health uses, pet food, or the like, with the above functions shown thereon as necessary.

The kind of drink or food products described above is not particularly limited. Examples of the drink products include a wide variety of drink products such as fruit juice drinks, carbonated drinks, tea drinks, coffee drinks, milk drinks, alcoholic beverages, and soft drinks. The form of food products may be any form such as solid, semi-solid, or liquid, and may be a tablet form, pill form, tablet, capsule form, liquid form, syrup form, powder form, granule form, or the like. Examples of the food products include breads, noodles, pastas, jellied food products, various snacks, cakes, sweets, ice creams, soups, dairy products, frozen foods, instant food products, other processed food products, seasonings, supplements and the like. The type of the above feed is not particularly limited and may be for any animal, and the form can be any form as in the case of the above food products.

The drink or food products, feeds, or raw materials therefor, may comprise the above haguro-so or an extract thereof, or the formula (I) compound or a salt thereof, singly, or may comprise in combination with other food materials or additives such as a solvent, softener, oil, emulsifier, preservative, perfume, stabilizer, colorant, antioxidant, moisturizer, or thickener. The content of the above haguro-so or an extract thereof in the drink or food products or feeds is, on a dry weight basis, preferably from 0.0001 to 10% by mass, more preferably from 0.0001 to 5% by mass, even more preferably from 0.001 to 1% by mass. The content of the formula (I) compound or a salt thereof in the drink or food products or feeds is, on a formula (I) compound basis, preferably from $1.0 \times 10^{-10}$ to 0.01% by mass, more preferably from $1.0 \times 10^{-9}$ to 0.001% by mass, even more preferably from $1.0 \times 10^{-8}$ to $1.0 \times 10^{-4}$% by mass.

The present invention provides a method for inhibiting the dopa oxidase activity in cells. The method comprises a step of adding the above haguro-so or an extract thereof, or the formula (I) compound or a salt thereof, to a tyrosinase-expressing cell in which the dopa oxidase activity needs to be inhibited.

The present invention provides a method for inhibiting the melanin production caused by cells. The method comprises a step of adding the above haguro-so or an extract thereof, or the formula (I) compound or a salt thereof, to a melanin-producing cell in which the melanin production needs to be inhibited.

In the present invention, the "cell" in which the dopa oxidase activity or melanin production is to be inhibited is not particularly limited, insofar as it is a tyrosinase-expressing or melanin-producing cell that is native or modified by a genetic engineering technique. The cell is preferably pigment cells (melanocyte, retinal pigment epithelial cell, or the like), with melanocyte being more preferable.

Alternatively, the "cell" may be a cell debris or cell fraction of the cells mentioned above, tissues containing the cells mentioned above or cultured product derived from the cells mentioned above. When the cell is a cell cultured product, the cell is preferably cultured in the presence of the above haguro-so or an extract thereof, or the formula (I) compound or a salt thereof.

The concentration of the above haguro-so or an extract thereof to be added is, when the cell is a cell cultured product, as the final concentration in the cultured product, on a dry weight basis, from 0.00001 to 2% (w/v), preferably from 0.00005 to 0.5% (w/v), more preferably from 0.0001 to 0.1% (w/v).

In the present invention, the above haguro-so or an extract thereof, or the formula (I) compound or a salt thereof, can be administered or ingested in an effective amount to or by a subject for inhibiting the dopa oxidase activity, inhibiting the melanin production, whitening the skin, or preventing, ameliorating, or treating symptoms such as skin pigmentation, speckles, or freckles. The administration or ingestion may be carried out nontherapeutically for health promotion or aesthetic purpose.

Examples of the subject in the administration or ingestion include animals which need the inhibition of the dopa oxidase activity. Alternatively, examples of the subject in the administration or ingestion include animals who desire the melanin production inhibition or skin whitening, or animals who desire the prevention, amelioration, or treatment of the symptoms such as skin pigmentation, speckles, or freckles. The animal is preferably a human or non-human mammal, with a human being more preferable. In an aspect, the subject can be the tissues or cells of animals described above.

Accordingly, in still another aspect, the present invention provides a method for inhibiting the dopa oxidase activity comprising administration or ingestion of an effective amount of the formula (I) compound or a salt thereof to or by a subject who needs the dopa oxidase activity inhibition. The present invention also provides a method for inhibiting the melanin production comprising administration or ingestion of an effective amount of the formula (I) compound or a salt thereof to or by a subject who needs the melanin production inhibition. The present invention also provides a method for whitening the skin comprising administration or ingestion of an effective amount of the formula (I) compound or a salt thereof to or by a subject who needs the skin whitening.

In another aspect, the present invention provides a method for inhibiting the dopa oxidase activity comprising administration or ingestion of an effective amount of haguro-so or an organic solvent extract thereof to or by a subject who needs the dopa oxidase activity inhibition. The present invention also provides a method for inhibiting the melanin production comprising administration or ingestion of an effective amount of haguro-so or an organic solvent extract thereof to or by a subject who needs the melanin production inhibition. The present invention also provides a method for whitening the skin comprising administration or ingestion of an effective amount of haguro-so or an organic solvent extract thereof to or by a subject who needs the skin whitening.

The preferable amount of administration or ingestion is variable depending on species, body weight, sex, age, conditions of the subject, or other factors. The dose, route, interval of administration or injection, and the amount of ingestion and interval, can be suitably determined by those skilled in the art. For example, when topically administered to the human skin, the amount of administration per adult (60 kg) is preferably from 0.001 to 1 mg/day, more preferably from 0.01 to 0.1 mg/day, on a dry weight basis of haguro-so or an extract thereof. The formula (I) compound or a salt thereof is preferably administered, on a formula (I) compound basis, in an amount of from $1.0 \times 10^{-7}$ to 0.1 mg/day, more preferably from $1.0 \times 10^{-6}$ to 0.001 mg/day.

EXAMPLES

The present invention is described below in further detail with reference to Examples, but is not limited thereto.

Production Example

Preparation of a Haguro-So Extract

Production Example 1

Preparation of a Haguro-So Water Extract 500 mL of water was added to 50 g of haguro-so (manufactured by SHINWA BUSSAN CO., LTD.), and a crude extract liquid was obtained by extraction at 60° C. for 5 hours and filtration, and subsequently freeze-dried, yielding 0.67 g of an extracted solid. The extracted solid was dissolved in 10% ethanol to give an evaporation residue of 1.0 w/v %, thereby preparing a haguro-so water extract.

Production Example 2

Preparation of a Haguro-So 50% Ethanol Extract 500 mL of 50% ethanol was added to 50 g of haguro-so (manufactured by SHINWA BUSSAN CO., LTD.), and a crude extract liquid was obtained by extraction at room temperature for 5 days and filtration, and subsequently concentrated and solidified to dryness, yielding 3.97 g of an extracted solid. The extracted solid was dissolved in 50% ethanol to give an evaporation residue of 1.0 w/v %, thereby preparing a haguro-so 50% ethanol extract.

Production Example 3

Preparation of a Haguro-So 95% Ethanol Extract 500 mL of 95% ethanol was added to 50 g of haguro-so (manufactured by SHINWA BUSSAN CO., LTD.), and a crude extract liquid was obtained by extraction at room temperature for 5 days and filtration, and subsequently concentrated and solidified to dryness, yielding 1.01 g of an extracted solid. The extracted solid was dissolved in 95% ethanol to give an evaporation residue of 1.0 w/v %, thereby preparing a haguro-so 95% ethanol extract.

Example 1

Dopa Oxidase Activity Inhibition by the Haguro-So Extract (1) Cell Culture

Normal human neonatal epidermal melanocytes (NHEMs; KURABO INDUSTRIES, LTD.) were seeded in a 96-well plates at a density of $1 \times 10^4$ cells/well (100 L/well) and cultured at 37° C. under a 5% $CO_2$. Cells were maintained in Medium 254 (KURABO INDUSTRIES, LTD.) containing growth supplement (HMGS) without PMA.

After 3-day culture, the haguro-so extracts (water extract, 50% ethanol extract, or 95% ethanol extract) prepared in accordance with the above Production Examples 1 to 3 and having an evaporation residue of 1.0 w/v % were each added to give a final concentration shown in Table 1 together with Endothelin-1 (ET-1), SCF, α-MSH, Histamine, and $PGE_2$ adjusted to have a final concentration of 1 nM in each medium, and cultured under the conditions of 37° C. and a 5% $CO_2$ for 3 days. For a control, an ethanol aqueous solution (10%, 50%, or 95%) of the equal amount was added.

(2) Measurement of Dopa Oxidase Activity

After completion of culture, Alamar Blue (Invitrogen) reagent was added in an amount of 20 μL/well and incubated for 2 to 3 hours, followed by measuring the fluorescence intensity of the medium to measure the cellular respiration activity. Subsequently, the cells were washed with PBS, an extraction buffer (0.1 M Tris-HCL (pH 7.2), 1% NP-40, 0.01% SDS, 100 μM PMSF, 1 μg/m aprotinin) was added in an amount of 20 μL/well, and an assay buffer (4% dimethylformamide, 100 mM sodium phosphate-buffered (pH 7.1)) was added in an amount of 20 μL/well, in which the cells were solubilized at 4° C. for 3 hours, thereby the dopa oxidase activity was measured. The dopa oxidase activity was measured by the following method with reference to the MBTH method (Winder A. et al., 1991, Eur. J. Biochem. 198: 317-326).

To each of the wells containing the solubilized cell solution, 80 μL of the above assay buffer, 60 μL of 20.7 mM MBTH (3-methyl-2-benzothiazolinon hydrazone) solution, and 40 μL of 5 mM L-dopa(L-dihydroxyphenylalanine) solution as a substrate were added, reacted at 37° C. for 30 to 60 minutes, thereby measuring the color reaction thereof at 490 nm absorbance (N=3). The measured values were shown in the relative value to the result of the control.

(3) Results

Table 1 and FIG. 1 show the results. The dopa oxidase activity was inhibited by the haguro-so 50% ethanol extract and 95% ethanol extract in an extract addition concentration-dependent manner. The cellular respiration activity measurement by the Alamar Blue method confirmed that the haguro-so extract addition at the concentrations shown in Table 1 does not affect the cell growth.

TABLE 1

| Plant | Solvent | Amount added (v/v %) | Extract final concentration (w/v %) | Dopa oxidase activity (%) |
|---|---|---|---|---|
| Haguro-so | Water | 0.005 | 0.00005 | 107.9 |
| | | 0.01 | 0.0001 | 105.3 |
| | | 0.02 | 0.0002 | 109.2 |
| | | 0.05 | 0.0005 | 105.6 |
| | | 0.1 | 0.001 | 100.6 |
| | 50% EtOH | 0.005 | 0.00005 | 110.0 |
| | | 0.01 | 0.0001 | 109.7 |
| | | 0.02 | 0.0002 | 96.8 |
| | | 0.05 | 0.0005 | 45.6 |
| | | 0.1 | 0.001 | 32.9 |
| | | 0.2 | 0.002 | 19.4 |
| | 95% EtOH | 0.005 | 0.00005 | 90.4 |
| | | 0.01 | 0.0001 | 55.8 |
| | | 0.02 | 0.0002 | 36.3 |
| | | 0.05 | 0.0005 | 23.8 |

Example 2

Melanin Production Inhibition by a Haguro-So Extract

Using EPI-100-NMM113 medium to which ET-1 and SCF were added to give a final concentration of 10 nM, a 3D cultured skin model (MEL300A) was cultured under the conditions of 37° C. and a 5% $CO_2$. On the first day of the culture, the haguro-so 50% ethanol extract prepared in accordance with the Production Example 2 and having an evaporation residue of 1.0 w/v % was added to give a final concentration of 0.1 v/v % (extract final concentration of 0.001 w/v %). For a control, a 50% ethanol of the equal amount was added. The medium was exchanged every 3 days. 14 Days later, the cellular respiration activity was measured in the same manner as in Example 1 using the Alamar Blue reagent. Subsequently, the 3D cultured skin was washed with PBS while kept in a cup, which was an incubation substrate, and the skin sheet was then peeled and transferred to a tube using a pair of tweezers, and further washed 3 times with PBS. The skin sheet was washed 3 times with 50% ethanol and twice with 100% ethanol, and allowed to stand at room temperature overnight until completely dried. After finally adding 200 μL of 2M NaOH, the skin sheet was dissolved at 100° C., and the supernatant obtained by centrifugal separation was measured for the absorbance at a measurement wavelength of 405 nm to calculate an amount of melanin. The measured value was shown in the relative value to the result of the control.

Figure 2:
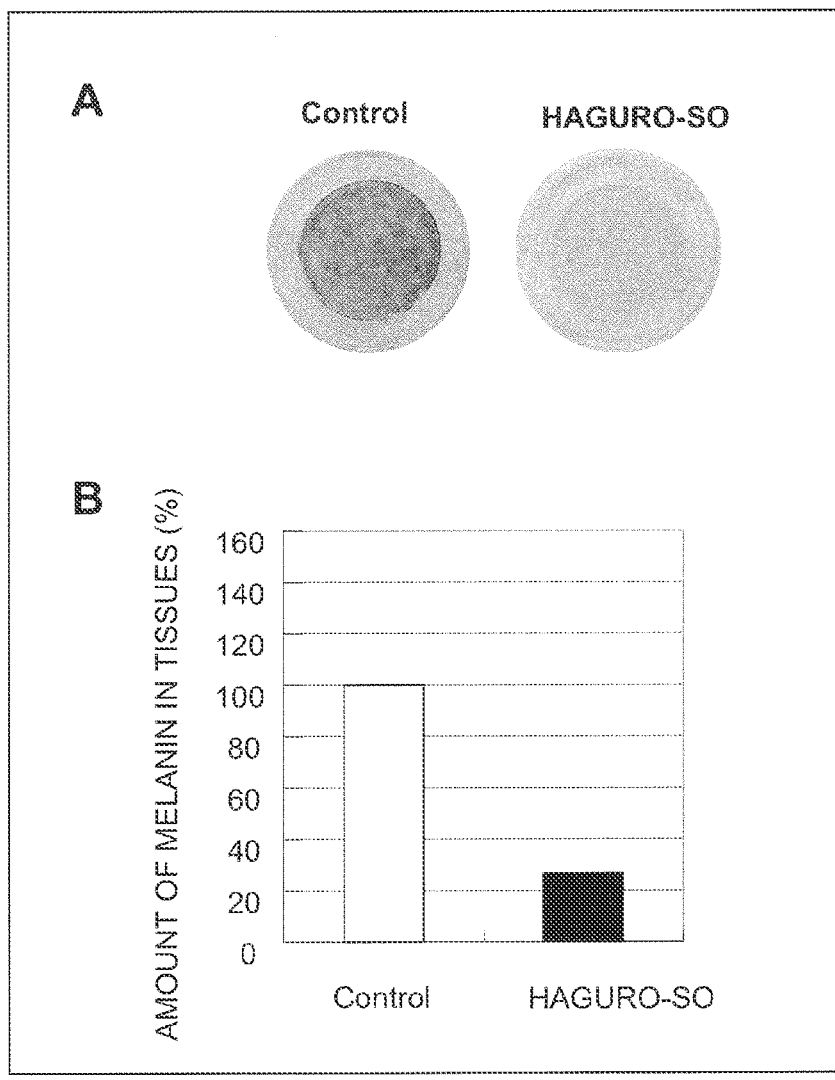
FIG. 2 shows the melanin production inhibition by the haguro-so extract. A: Photo of cultured skin, B: amount of melanin in cultured skin.

FIG. 2 shows the photo of 3D cultured skin model on day 14 of the culture and the measurement results of the amount of melanin. The cell darkening inhibitory effect by the haguro-so extract addition was visually assured (FIG. 2A), and the amount of melanin in the cells reduced 70% or more (FIG. 2B). Further, the cellular respiration activity measurement by the Alamar Blue method confirmed that the extract at this concentration is not cytotoxic.

Production Example 4

Preparation of the Formula (I) Compound 500 g of haguro-so was extracted with 50% ethanol (5 L) and the solvent was concentrated, thereby obtaining 44 g of an extracted solid. The obtained extracted solid was subjected to a liquid-liquid distribution using water and ethyl acetate, thereby obtaining 4.7 g (yield 11%) of an ethyl acetate layer. The dopa oxidase activities of the water layer and ethyl acetate layer were measured in the same procedure as in Example 1 to be described later, and the activity was confirmed to have been concentrated in the ethyl acetate layer.

The ethyl acetate layer was further fractionated using a silica gel column. The silica gel column used was a Hi-Flush column (4 L, manufactured by YAMAZEN CORPORATION). After flushing with 100% hexane for 10 minutes, the layer was eluted with a hexane-ethyl acetate gradient ramping from a 0% to 100% ethyl acetate ratio over 60 minutes, subsequently with an ethyl acetate-methanol gradient ramping from a 0% to 10% methanol ratio over 30 minutes, and finally with 100% methanol over 30 minutes. After fractionating every 2 minutes by flushing at a flow rate of 30 mL/min, each of the fractions was analyzed by TLC and those having similar Rf values were combined, thereby obtaining 7 fractions. Each fraction was measured for the dopa oxidase activity by the above procedure, and it was found that the activity was concentrated in the 2 fractions, fraction (4) (0.8 g, yield 1.8%) and fraction (7) (1.91 g, yield 4.3%). In fraction (4), the dopa oxidase activity was further confirmed to have been concentrated in the precipitate caused by the addition of MeOH.

The precipitate was fractionated by HPLC. The column, Inertsil ODS-3 (14×250 mm, manufactured by GL Sciences Inc.) was used. Elution was carried out over 20 minutes at a flow rate of 15 mL/min, at a detection wavelength of 254 nm, with 0.1% formic acid aqueous solution-acetonitrile, at a 50% acetonitrile ratio, thereby obtaining 2 major peaks. Each of the peaks was separately collected and defined as fraction (8) and fraction (9). The dopa oxidase activity was found in both fraction (8) (48 mg, yield 0.38%) and fraction (9) (58 mg, yield 0.46%).

The fraction (7) was further fractionated using 470 mg thereof by HPLC. The column, Inertsil ODS-3 (10×250 mm, manufactured by GL Sciences Inc.), was eluted over 20 minutes at a flow rate of 7.5 mL/min, at a detection wavelength of 254 nm, with 0.1% formic acid aqueous solution-acetonitrile, at a 35% acetonitrile ratio. The fraction was fractionated accordingly to the peak, fraction (10), fraction (11), and fraction (12) were obtained, and the dopa oxidase activity was found in fraction (11) (14.1 mg, yield 0.13%).

The above fraction (8), fraction (9), and fraction (11) were each analyzed for the NMR structure, and, as shown in Tables 2 to 4 below, fraction (8) was identified as justicidin B, fraction (9) was identified as justicidin A, and fraction (11) was identified as tuberculatin.

TABLE 2

Fraction (8): (Measuring solvent: Deuterated chloroform)

|  | 13C | | 1H | |
| --- | --- | --- | --- | --- |
|  | Isolated product | Literature value | Isolated product | Literature value |
| 1 | 139.4 | 139.7 |  |  |
| 2 | 118.4 | 118.6 |  |  |
| 3 | 139.5 | 139.7 |  |  |
| 4 | 118.2 | 118.5 | 7.71 | 7.71 |
| 5 | 105.9 | 106.1 | 7.19 | 7.19 |
| 6 | 151.7 | 151.9 |  |  |
| 7 | 149.9 | 150.2 |  |  |
| 8 | 105.7 | 105.9 | 7.11 | 7.12 |
| 9 | 128.7 | 129 |  |  |
| 10 | 133.1 | 133.3 |  |  |
| 11 | 169.9 | 169.9 |  |  |
| 12 | 68 | 68.2 | 5.38 | 5.39 |
| 1' | 128.3 | 128.5 |  |  |
| 2' | 110.5 | 110.7 | 6.86 | 6.86 |
| 3' | 147.5 | 147 |  |  |
| 4' | 147.4 | 147 |  |  |
| 5' | 108.1 | 108.4 | 6.97 | 6.98 |
| 6' | 123.4 | 123.6 | 6.84 | 6.84 |
| 7' | 101.2 | 101.4 | 6.05, 6.1 | 6.05, 6.1 |
| 6-OMe | 56 | 56.2 | 4.05 | 4.06 |
| 7-OMe | 55.8 | 56 | 3.82 | 3.82 |

Literature value: Tetrahedron, 2002, 58: 5989-6001

TABLE 3

Fraction (9): (Measuring solvent: Deuterated chloroform)

|  | 13C | | 1H | |
| --- | --- | --- | --- | --- |
|  | Isolated product | Literature value | Isolated product | Literature value |
| 1 | 134.5 | 134.4 |  |  |
| 2 | 119.4 | 119.3 |  |  |
| 3 | 124.5 | 124.5 |  |  |
| 4 | 147.9 | 147.5 |  |  |
| 5 | 100.7 | 100.6 | 7.54 | 7.55 |
| 6 | 151.7 | 151.6 |  |  |
| 7 | 150.4 | 150.3 |  |  |
| 8 | 106.2 | 106.2 | 7.05 | 7.09 |

TABLE 3-continued

Fraction (9): (Measuring solvent: Deuterated chloroform)

|  | 13C | | 1H | |
|---|---|---|---|---|
|  | Isolated product | Literature value | Isolated product | Literature value |
| 9 | 130.7 | 126 | | |
| 10 | 126 | 130.6 | | |
| 11 | 169.7 | 169.5 | | |
| 12 | 66.8 | 66.6 | 5.54 | 5.55 |
| 1' | 128.6 | 128.5 | | |
| 2' | 110.9 | 110.8 | 6.82 | 6.81 |
| 3' | 147.6 | 147.4 | | |
| 4' | 147.5 | 147.4 | | |
| 5' | 108.3 | 108.1 | 6.95 | 6.95 |
| 6' | 123.7 | 123.6 | 6.79 | 6.77 |
| 7' | 101.3 | 101.2 | 6.04, 6.09 | 6.04, 6.06 |
| 4-OMe | 59.8 | 59.6 | 4.13 | 4.12 |
| 6-OMe | 55.9 | 56.3 | 3.8 | 3.8 |
| 7-OMe | 56.3 | 55.9 | 4.07 | 4.08 |

Literature value: Journal of Natural products, 1999, 62: 1056-1058
Journal of Natural products, 1986, 49: 348-350
Note:
in Table, NMR values under 13C at the ninth position and the tenth position are inverted between Isolated product and Literature value. The values under Isolated product are considered to be more reliable since the structure analysis in Isolated product is confirmed by the INADEQUATE measurement.

TABLE 4

Fraction (11): (Measuring solvent: Deuterated chloroform)

|  | 13C | | 1H | |
|---|---|---|---|---|
|  | Isolated product | Literature value | Isolated product | Literature value |
| 1 | 136.9 | 137.1 | | |
| 2 | 120.1 | 126.5 | | |
| 3 | 130.1 | 130.1 | | |
| 4 | 146.4 | 146.4 | | |
| 5 | 102.0 | 101.7 | 7.58 | 7.75 |
| 6 | 153.3 | 153.8 | | |
| 7 | 151.8 | 152.1 | | |
| 8 | 107.1 | 107 | 6.97 | 7.11 |
| 9 | 131.8 | 132 | | |
| 10 | 128.4 | 128.6 | | |
| 11 | 172.3 | 171.8 | | |
| 12 | 68.9 | 68.7 | 5.44 | 5.54 |
|  |  |  | 5.51 | 5.60 |
| 1' | 130.3/130.4 | 130.1 | | |
| 2' | 111.9/112.0 | 111.7 | 6.7 | 6.85 |
| 3' | 149.1 | 149.2 | | |
| 4' | 149.1 | 149.2 | | |
| 5' | 109.07/109.09 | 108.2 | 6.9 | 6.99 |
| 6' | 124.9/125.0 | 124.7 | 6.7 | 6.81 |
| 7' | 102.7 | 102.4 | 6.0 | 6.07 |
|  |  |  | 6.02 | 6.09 |
| 6-OMe | 56.6 | 56.2 | 3.960/3.965 | 4.06 |
| 7-OMe | 56.1 | 55.7 | 3.679/3.682 | 3.77 |
| 1" | 112.97/113.0 | 112.9 | 5.45 | 5.57 |
| 2" | 78.8 | 78.5 | 4.49 | 4.56 |
| 3" | 80.4 | 79.5 | | |
| 4" | 76.1 | 75.7 | 3.9 | 3.97 |
|  |  |  | 4.31 | 4.38 |
| 5" | 64.3 | 64.2 | 3.66 | 3.71 |

Literature value: Chemical & Pharmaceutical Bulletin, 2002, 50: 844-846

Example 3

Dopa Oxidase Activity Inhibition by the Formula (I) Compound

Normal human neonatal epidermal melanocytes (NHEMs; KURABO INDUSTRIES, LTD.) were inoculated in a 96-well plate in a cell density of $1 \times 10^4$ cells/well (100 µL/well) and cultured at 37° C. under a 5% $CO_2$. The medium used was Medium 254 containing PMA(−) growth supplement (HMGS).

After 3-day culture, each of the compounds shown in Table 4 was added to give final concentrations shown in the same Table, together with Endothelin-1 (ET-1), SCF, α-MSH, Histamine, and $PGE_2$ adjusted to give a final concentration of 1 nM in each medium, and cultured under the conditions of 37° C. and a 5% $CO_2$ for 3 days. For a control, a DMSO solution of the equal amount was added.

After completion of the culture, Alamar Blue (Invitrogen) reagent was added in an amount of 20 μL/well and incubated for 2 to 3 hours, followed by measuring the fluorescence intensity of the medium to measure the cellular respiration activity. Subsequently, the cells were washed with PBS, an extraction buffer (0.1 M Tris-HCL (pH 7.2), 1% NP-40, 0.01% SDS, 100 μM PMSF, 1 μg/m aprotinin) was added in an amount of 20 μL/well and an assay buffer (4% dimethylformamide, 100 mM sodium phosphate-buffered (pH 7.1)) was added in an amount of 20 μL/well, in which the cells were solubilized at 4° C. for 3 hours, thereby the dopa oxidase activity was measured. The dopa oxidase activity was measured by the following method with reference to the MBTH method (Winder A. et al., Eur. J. Biochem., 1991, 198: 317-326).

To each of the wells containing the solubilized cell solution, 80 μL of the above assay buffer, 60 μL of 20.7 mM MBTH (3-methyl-2-benzothiazolinon hydrazone) solution and 40 μL of 5 mM L-dopa (L-dihydroxyphenylalanine) solution as a substrate were added, reacted at 37° C. for 30 to 60 minutes, thereby measuring the color reaction thereof at 490 nm absorbance (N=3). The measured values were shown in the relative value to the result of the control.

Table 5 shows the results. The dopa oxidase activity was inhibited by the formula (I) compound in an extract addition concentration-dependent manner. The cellular respiration activity measurement by the Alamar Blue method confirmed that the compound addition at the concentrations shown in Table 5 does not affect the cell growth.

TABLE 5

| No. | Structure | Name | Source | Evaluation concentration (μM) | Dopa oxidase inhibitory rate (%) |
|---|---|---|---|---|---|
| 1 | | Justicidin A | Production Example 1 | 0.1<br>0.5<br>0.1 | 20<br>50<br>55 |
| 2 | | Justicidin B | Production Example 1 | 0.1<br>0.5<br>1.0 | 10<br>30<br>50 |
| 3 | | Tuberculatin | Production Example 1 | 0.1<br>0.5<br>1.0 | 45<br>50<br>70 |

TABLE 5-continued

| No. | Compound Structure | Name | Source | Evaluation concentration (μM) | Dopa oxidase inhibitory rate (%) |
|---|---|---|---|---|---|
| 4 | (structure) | Diphyllin | Pharmeks LTD | —<br>0.5<br>1.0 | —<br>20<br>40 |
| 5 | (structure) | 4-Ethoxy-6,7-dimethoxy-9-(1,3-benzodioxol-5-yl)naphtho[2,3-c]furan-1(3H)-one | Pharmeks LTD | 0.1<br>0.5<br>— | 40<br>60<br>— |
| 6 | (structure) | 4-Acetoxy-6,7-dimethoxy-9-(1,3-yl)naphtho[2,3-c]furan-1(3H)-one | Pharmeks LTD | —<br>0.5<br>1.0 | —<br>40<br>50 |
| 7 | (structure) | Justicidin F | ChromaDex | 0.1<br>—<br>— | 20<br>—<br>— |

Example 4

Melanin Production Inhibition by the Formula (I) Compound

Using EPI-100-NMM113 medium to which ET-1 and SCF were added to give a final concentration of 10 nM, a 3D cultured skin model (MEL300A) was cultured under the conditions of 37° C. and a 5% CO$_2$. On the first day of the culture, a 100% DMSO solution of each compound was added to give a final concentration of 0.5 μM. For a control, a DMSO solution of the equal amount was added. The medium was exchanged every 3 days. 14 Days later, the cellular respiration activity was measured using the Alamar Blue reagent. Subsequently, the 3D cultured skin was washed with PBS while kept in a cup, which was an incubation substrate, and the skin sheet was then peeled and transferred to a tube using a pair of tweezers, and further washed 3 times with PBS. The skin sheet was washed 3 times with 50% ethanol and twice with 100% ethanol, and allowed to stand at room temperature overnight until completely dried. After finally adding 200 μL of 2M NaOH, the skin sheet was dissolved at 100° C., and the supernatant obtained by centrifugal separation was measured for the absorbance at a measurement wavelength of 405 nm to calculate an amount of melanin. The measured values were shown in the relative value to the result of the control.

Figure 3:
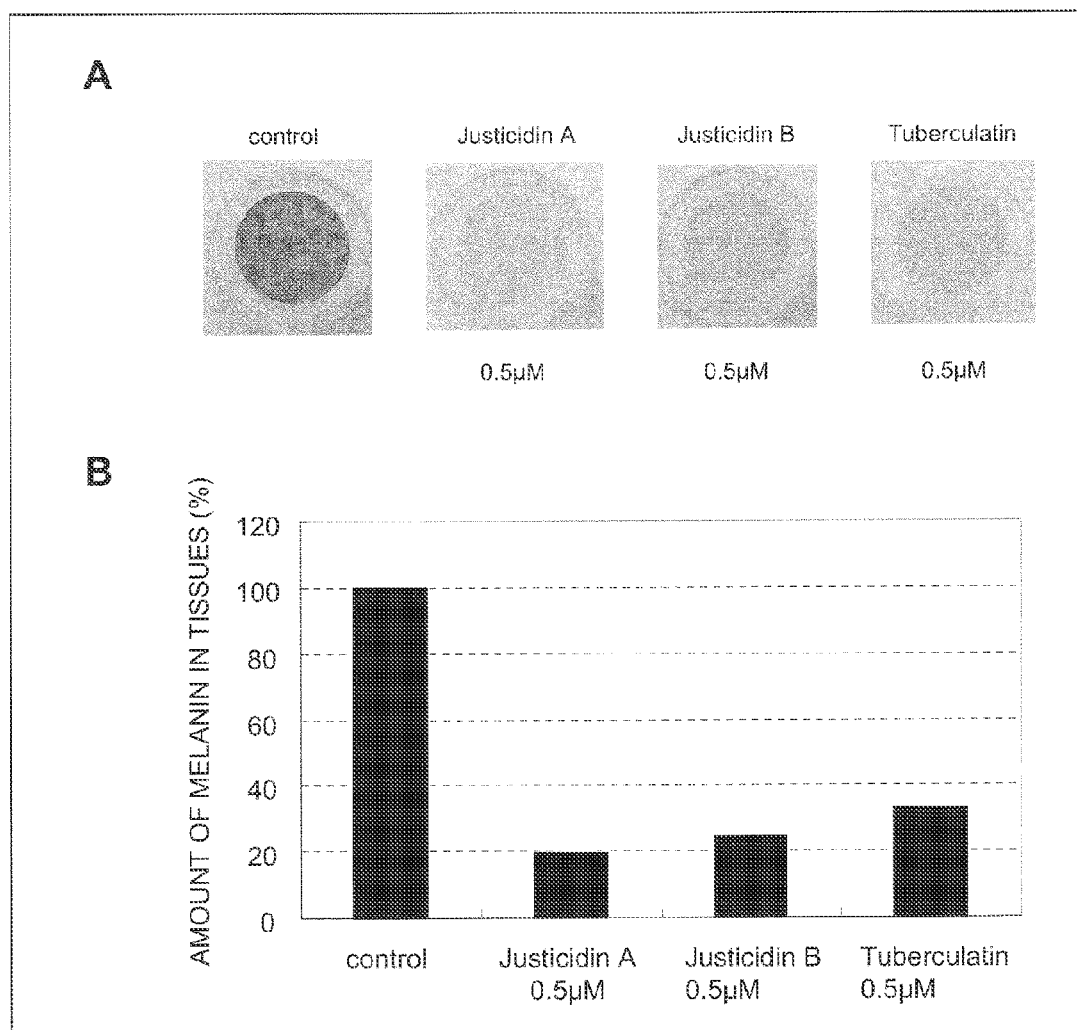
FIG. 3 shows the melanin production inhibition by the compounds of the present invention. A: Photos of cultured skins, B: amount of melanin in cultured skins.

FIG. 3 shows the photos of 3D cultured skin models on day 14 of the culture and the measurement results of the amount of melanin. The cell darkening inhibitory effect by the formula (I) compound addition was visually assured (FIG. 3A), and the amount of melanin in the cells reduced 60% or more (FIG. 3B). Further, the cellular respiration activity measurement by the Alamar Blue method confirmed that the extract at this concentration is not cytotoxic.

What is claimed is:

1. A method for inhibiting dopa oxidase activity in a subject's skin cells, comprising administration or ingestion, to or by the subject, of a composition that comprises an effective amount of a dopa oxidase inhibitor that consists essentially of an organic solvent extract of haguro-so, wherein the subject is in need of inhibiting dopa oxidase activity in the subject's skin cells.

2. A method for inhibiting melanin production in a subject's skin cells, comprising administration or ingestion, to or by the subject, of a composition that comprises an effective amount of a melanin production inhibitor that consists essentially of an organic solvent extract of haguro-so, wherein the subject is in need of inhibiting melanin production in the subject's skin cells.

3. A method for whitening a subject's skin comprising administration or ingestion, to or by the subject, of a composition that comprises an effective amount of a dopa oxidase inhibitor or a melanin production inhibitor, the inhibitor consisting essentially of an organic solvent extract of haguro-so, wherein the subject is in need of whitening of the subject's skin.

4. A method for inhibiting dopa oxidase activity in a human subject's skin cells, comprising administration or ingestion, to or by the subject, of a composition that comprises an effective amount of a dopa oxidase inhibitor that consists essentially of a compound represented by the following formula (I) or a salt thereof, wherein the subject is in need of inhibiting dopa oxidase activity in the subject's skin cells and wherein formula (I) is:

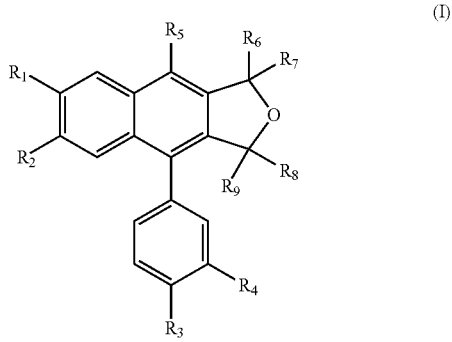

(I)

wherein,
$R_1$ and $R_2$, being the same or different, each represent a hydroxyl group, or a $C_{1-4}$ linear or branched alkoxy group, or $R_1$ and $R_2$ together form a methylenedioxy group;
$R_3$ and $R_4$, being the same or different, each represent a hydroxyl group, or a $C_{1-4}$ linear or branched alkoxy group, or $R_3$ and $R_4$ together form a methylenedioxy group;
$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy, and (3-O-methyl-β-D-glucopyranosyl)oxy,
$R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

5. The method according to claim 4, wherein $R_1$ and $R_2$ both represent a $C_{1-4}$ linear or branched alkoxy group and $R_3$ and $R_4$ together form a methylenedioxy group, or $R_1$ and $R_2$ together form a methylenedioxy group and $R_3$ and $R_4$ both represent a $C_{1-4}$ linear or branched alkoxy group.

6. The method according to claim 4, wherein the $C_{1-4}$ linear or branched alkoxy group represented by $R_1$ to $R_4$ is methoxy.

7. The method according to claim 4, wherein $R_5$ is a hydrogen atom, a hydroxyl group, methoxy, ethoxy, acetyloxy, or (D-apio-β-D-furanosyl)oxy.

8. The method of claim 4, wherein the composition is administered and the composition is an external agent for skin.

9. The method of claim 4, wherein the composition contains $1.0 \times 10^{-10}$ to 0.01% of the compound of formula (I) or salt thereof.

10. A method for inhibiting melanin production in a human subject's skin cells, comprising administration or ingestion, to or by the subject, of a composition that comprises an effective amount of a melanin production inhibitor that consists essentially of a compound represented by the following formula (I) or a salt thereof, wherein the subject is in need of inhibiting melanin production in the subject's skin cells and wherein formula (I) is:

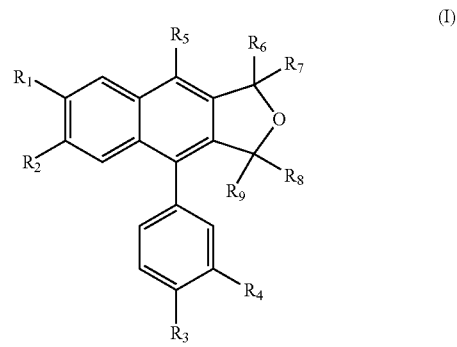

(I)

wherein,
$R_1$ and $R_2$, being the same or different, each represent a hydroxyl group, or a $C_{1-4}$ linear or branched alkoxy group, or $R_1$ and $R_2$ together form a methylenedioxy group;
$R_3$ and $R_4$, being the same or different, each represent a hydroxyl group, or a $C_{1-4}$ linear or branched alkoxy group, or $R_3$ and $R_4$ together form a methylenedioxy group;

$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy, and (3-O-methyl-β-D-glucopyranosyl)oxy, $R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

11. The method according to claim 10, wherein $R_1$ and $R_2$ both represent a $C_{1-4}$ linear or branched alkoxy group and $R_3$ and $R_4$ together form a methylenedioxy group, or $R_1$ and $R_2$ together form a methylenedioxy group and $R_3$ and $R_4$ both represent a $C_{1-4}$ linear or branched alkoxy group.

12. The method according to claim 10, wherein the $C_{1-4}$ linear or branched alkoxy group represented by $R_1$ to $R_4$ is methoxy.

13. The method according to claim 10, wherein $R_5$ is a hydrogen atom, a hydroxyl group, methoxy, ethoxy, acetyloxy, or (D-apio-β-D-furanosyl)oxy.

14. The method of claim 10, wherein the composition is administered and the composition is an external agent for skin.

15. The method of claim 10, wherein the composition contains $1.0 \times 10^{-10}$ to 0.01% of the compound of formula (I) or salt thereof.

16. A method for whitening a human subject's skin comprising administration or ingestion, to or by the subject, of a composition that comprises an effective amount of a dopa oxidase inhibitor or a melanin production inhibitor, the inhibitor consisting essentially of a compound represented by the following formula (I) or a salt thereof, wherein the subject is in need of whitening of the subject's skin and wherein formula (I) is:

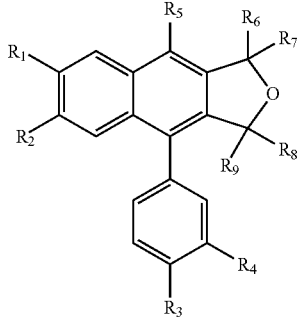

(I)

wherein,
$R_1$ and $R_2$, being the same or different, each represent a hydroxyl group, or a $C_{1-4}$ linear or branched alkoxy group, or $R_1$ and $R_2$ together form a methylenedioxy group;

$R_3$ and $R_4$, being the same or different, each represent a hydroxyl group, or a $C_{1-4}$ linear or branched alkoxy group, or $R_3$ and $R_4$ together form a methylenedioxy group;

$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O, 3-O,4-O-trimethyl-β-D-xylopyranosyl)oxy, and (3-O-methyl-β-D-glucopyranosyl)oxy, $R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

17. The method according to claim 16, wherein $R_1$ and $R_2$ both represent a $C_{1-4}$ linear or branched alkoxy group and $R_3$ and $R_4$ together form a methylenedioxy group, or $R_1$ and $R_2$ together form a methylenedioxy group and $R_3$ and $R_4$ both represent a $C_{1-4}$ linear or branched alkoxy group.

18. The method according to claim 16, wherein the $C_{1-4}$ linear or branched alkoxy group represented by $R_1$ to $R_4$ is methoxy.

19. The method according to claim 16, wherein $R_5$ is a hydrogen atom, a hydroxyl group, methoxy, ethoxy, acetyloxy, or (D-apio-β-D-furanosyl)oxy.

20. The method of claim 16, wherein the composition is administered and the composition is an external agent for skin.

21. The method of claim 16, wherein the composition contains $1.0 \times 10^{-10}$ to 0.01% of the compound of formula (I) or salt thereof.

22. A method for inhibiting dopa oxidase activity in a subject's skin cells, comprising administration or ingestion, to or by the subject, of a composition that comprises an effective amount of dopa oxidase inhibitors that consist essentially of a combination of (a) haguro-so or an organic solvent extract thereof and (b) an isolated compound represented by the following formula (I) or salt thereof, wherein the subject is in need of inhibiting dopa oxidase activity in the subject's skin cells and wherein formula (I) is

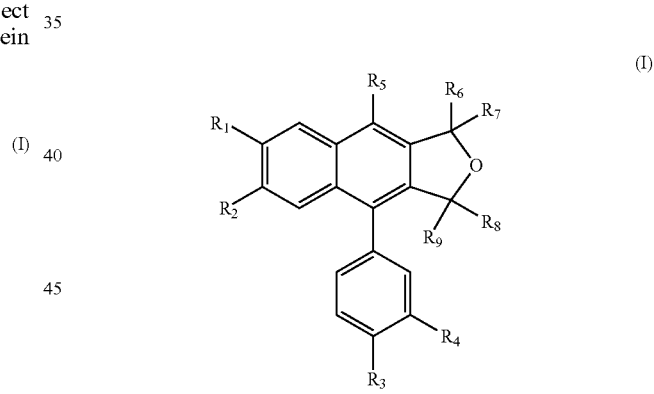

(I)

wherein the composition contains from $1.0 \times 10^{-10}$ to 0.01% by mass of the isolated compound of formula (I) or salt thereof, and wherein,
$R_1$ and $R_2$, being the same or different, each represent a hydroxyl group, or a $C_{1-4}$ linear or branched alkoxy group, or $R_1$ and $R_2$ together form a methylenedioxy group;

$R_3$ and $R_4$, being the same or different, each represent a hydroxyl group, or a $C_{1-4}$ linear or branched alkoxy group, or $R_3$ and $R_4$ together form a methylenedioxy group;

$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O, 3-O,4-O-trimethyl-β-D-xylopyranosyl)oxy, and (3-O-methyl-β-D-glucopyranosyl)oxy, $R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

23. A method for inhibiting melanin production in a subject's skin cells, comprising administration or ingestion, to or by the subject, of a composition that comprises an effective amount of melanin production inhibitors that consist essentially of a combination of (a) haguro-so or an organic solvent extract thereof and (b) an isolated compound represented by the following formula (I) or salt thereof, wherein the subject is in need of inhibiting melanin production in the subject's skin cells and wherein formula (I) is

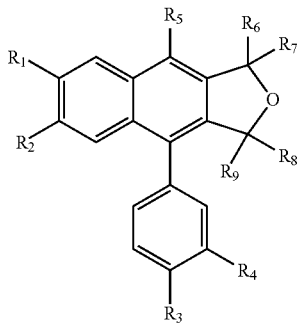
(I)

wherein the composition contains from $1.0 \times 10^{-10}$ to 0.01% by mass of the isolated compound of formula (I) or salt thereof, and wherein $R_1$ and $R_2$, being the same or different, each represent a hydroxyl group, or a $C_{1-4}$ linear or branched alkoxy group, or $R_1$ and $R_2$ together form a methylenedioxy group;

$R_3$ and $R_4$, being the same or different, each represent a hydroxyl group, or a $C_{1-4}$ linear or branched alkoxy group, or $R_3$ and $R_4$ together form a methylenedioxy group;

$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy, and (3-O-methyl-β-D-glucopyranosyl)oxy, $R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

24. A method for whitening a subject's skin comprising administration or ingestion, to or by the subject, of a composition that comprises an effective amount of dopa oxidase inhibitors or melanin production inhibitors, the inhibitors consisting essentially of a combination of (a) haguro-so or an organic solvent extract thereof and (b) an isolated compound represented by the following formula (I) or salt thereof, wherein the subject is in need of whitening of the subject's skin and wherein formula (I) is

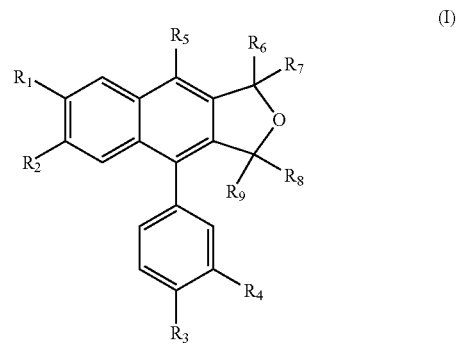
(I)

wherein the composition contains from $1.0 \times 10^{-10}$ to 0.01% by mass of the isolated compound of formula (I) or salt thereof, and wherein, $R_1$ and $R_2$, being the same or different, each represent a hydroxyl group, or a $C_{1-4}$ linear or branched alkoxy group, or $R_1$ and $R_2$ together form a methylenedioxy group;

$R_3$ and $R_4$, being the same or different, each represent a hydroxyl group, or a $C_{1-4}$ linear or branched alkoxy group, or $R_3$ and $R_4$ together form a methylenedioxy group;

$R_5$ represents a hydrogen atom, a hydroxyl group, a $C_{1-5}$ linear or branched alkoxy group, a $C_{1-4}$ acyl group, or a sugar residue selected from the group consisting of (D-apio-β-D-furanosyl)oxy, (β-D-glucopyranosyl)oxy, (3-O,4-O-dimethyl-D-xylopyranosyl)oxy, (2-O,3-O,4-O-trimethyl-β-D-xylopyranosyl)oxy, and (3-O-methyl-β-D-glucopyranosyl)oxy, $R_6$ and $R_7$ are each a hydrogen atom and $R_8$ and $R_9$ together represent an oxygen atom, or $R_8$ and $R_9$ are each a hydrogen atom and $R_6$ and $R_7$ together represent an oxygen atom.

* * * * *